United States Patent
Dang et al.

(10) Patent No.: US 7,101,568 B2
(45) Date of Patent: Sep. 5, 2006

(54) METHODS AND COMPOSITIONS FOR TREATING SOLID TUMORS

(75) Inventors: Wenbin Dang, Belle Mead, NJ (US); Robert Garver, Jr., Hoover, AL (US)

(73) Assignee: Guilford Pharmaceuticals, Inc., Baltimore, MD (US)

( * ) Notice: Subject to any disclaimer, the term of this patent is extended or adjusted under 35 U.S.C. 154(b) by 139 days.

(21) Appl. No.: 10/357,292

(22) Filed: Feb. 3, 2003

(65) Prior Publication Data

US 2003/0203033 A1 Oct. 30, 2003

Related U.S. Application Data

(63) Continuation of application No. 09/276,866, filed on Mar. 26, 1999, now Pat. No. 6,537,585.

(51) Int. Cl.
*A61F 2/02* (2006.01)
*A61F 9/50* (2006.01)
*A61F 47/30* (2006.01)

(52) U.S. Cl. .............. 424/426; 424/501; 424/502; 514/772.3

(58) Field of Classification Search .............. 424/501, 424/502, 426; 514/772.3
See application file for complete search history.

(56) References Cited

U.S. PATENT DOCUMENTS

| | | | |
|---|---|---|---|
| 3,271,329 A | 9/1966 | Coover et al. | |
| 3,442,982 A | 5/1969 | Friedman | |
| 3,927,231 A | 12/1975 | Desitter et al. | |
| 3,932,566 A | 1/1976 | Reader | |
| 4,100,354 A | 7/1978 | Owen | |
| 4,259,222 A | 3/1981 | Login et al. | |
| 4,328,174 A | 5/1982 | Schmidt et al. | |
| 4,474,937 A | 10/1984 | Bales | |
| 4,481,353 A | 11/1984 | Nyilas et al. | |
| 4,757,128 A | 7/1988 | Domb et al. | |
| 4,789,724 A | 12/1988 | Domb et al. | |
| 4,978,332 A | 12/1990 | Luck et al. | |
| 5,162,115 A | 11/1992 | Pietnegro | |
| 5,194,581 A | 3/1993 | Leong | |
| 5,213,804 A | 5/1993 | Martin et al. | |
| 5,256,765 A | 10/1993 | Leong | |
| 5,304,377 A | 4/1994 | Yamada | |
| 5,429,634 A | 7/1995 | Narciso et al. | |
| 5,530,093 A | 6/1996 | Engelhardt et al. | |
| 5,626,862 A | 5/1997 | Brem et al. | |

(Continued)

FOREIGN PATENT DOCUMENTS

| | | |
|---|---|---|
| EP | 0 057 116 | 8/1982 |
| EP | 0 193 019 | 9/1986 |
| EP | 0 386 757 | 9/1990 |
| HU | P0001256 A | 10/1998 |
| HU | P0202670 A | 2/2002 |
| WO | WO 94/23699 | 10/1994 |
| WO | WO 95/17901 | 6/1995 |
| WO | WO 96/03984 | 2/1996 |

(Continued)

OTHER PUBLICATIONS

Alkan–Onyuksel et al., "A Mixed Micellar Formulation Suitable for the Parenteral Administration of Taxol," Pharmaceutical Research, 11(2):206–211 (1994).

(Continued)

*Primary Examiner*—Carlos A. Azpuru
(74) *Attorney, Agent, or Firm*—Foley Hoag, LLP

(57) ABSTRACT

A biodegradable polymer composition comprising:
(a) a poly(phosphoester) biodegradable polymer and
(b) at least one antineoplastic agent in an amount effective to inhibit the growth of a solid tumor, which
is suitable for intratumoral administration to treat a mammal having a solid tumor.

39 Claims, 12 Drawing Sheets

U.S. PATENT DOCUMENTS

| | | | |
|---|---|---|---|
| 5,637,085 A | | 6/1997 | Cardinale |
| 5,651,986 A | | 7/1997 | Brem et al. |
| 5,846,565 A | | 12/1998 | Brem et al. |
| 5,886,026 A | | 3/1999 | Hunter et al. |
| 5,912,225 A | | 6/1999 | Mao et al. |
| 5,952,451 A | | 9/1999 | Zhao |
| 5,993,856 A | | 11/1999 | Ragavan et al. |
| 6,008,318 A | * | 12/1999 | Zhao et al. ............... 528/400 |
| 6,028,163 A | | 2/2000 | Zhao |
| 6,153,212 A | | 11/2000 | Mao et al. |
| 6,166,173 A | | 12/2000 | Mao et al. |
| 6,322,797 B1 | | 11/2001 | Mao et al. |
| 6,350,464 B1 | * | 2/2002 | Dang ..................... 424/426 |
| 6,376,644 B1 | | 4/2002 | Mao et al. |
| 6,403,675 B1 | | 6/2002 | Dang et al. |
| 6,419,709 B1 | | 7/2002 | Mao et al. |
| 6,479,067 B1 | * | 11/2002 | Dang ..................... 424/426 |
| 6,485,737 B1 | | 11/2002 | Mao et al. |
| 6,600,010 B1 | | 7/2003 | Mao et al. |
| 6,641,833 B1 | | 11/2003 | Dang |
| 2002/0045668 A1 | | 4/2002 | Dang et al. |
| 2002/0137814 A1 | | 9/2002 | Dang et al. |
| 2002/0198135 A1 | | 12/2002 | Dang et al. |
| 2003/0133903 A1 | | 7/2003 | Dang et al. |
| 2003/0134892 A1 | | 7/2003 | Dang et al. |
| 2004/0071774 A1 | | 4/2004 | Dang |

FOREIGN PATENT DOCUMENTS

| | | |
|---|---|---|
| WO | WO 97/40085 | 10/1997 |
| WO | WO 98/42330 | 10/1998 |
| WO | WO 98/44020 | 10/1998 |
| WO | WO 98/44021 | 10/1998 |
| WO | WO 98/48859 | 11/1998 |
| WO | WO 98/58012 | 12/1998 |
| WO | WO 00/64437 | 4/1999 |
| WO | WO 00/19976 | 4/2000 |
| WO | WO 00/57852 | 5/2000 |
| WO | WO 00/416783 | 7/2000 |
| WO | WO 02/03957 | 1/2002 |

OTHER PUBLICATIONS

Auerbach et al., "Site–Specific Drug Delivery to the Lung," Polymers for Advanced Technologies, vol. 3:323–329.

Bao et al., "A Controlled Release Paclitaxel Formulation (PACLIMER™ delivery system) has Superior Efficacy to Paclitaxel in an Ovarian Cancer Survival Model," Proceeding of the American Association for Cancer Research (90th Annual Meeting, Apr. 10–14, 1999) vol. 40, Abstract No. 3850 (Mar. 15, 1999).

Bruin et al., "Biodegradable Lysine Diisocyanate–based Poly(glycolide–co–ε–caprolactone)–urethane Network in Artificial Skin," Biomaterials, 11(4):291–95 (1990).

Burt et al., "Controlled Delivery of Taxol from Microspheres Composes of a Blend of Ethylene–Vinyl Acetate Copolymer and Poly(d, l–lactic acid)," Cancer Letters, 88:73079 (1995).

Demetrick et al., "The Development of a Novel Intraperitoneal Tumor–Seeding Prophylactic," The American Journal of Surgery®, vol. 173, May 1997.

Dordunoo et al., "Release of Taxol from Poly(ε–caprolactone) Pastes: Effect of Water–Soluble Additives," Journal of Controlled Release, 44:87–94 (1997).

Fan, Chang–Lie et al., "Studies of the Drug Controlled–Release Materials of Polyphosphate Containing Tyrosine Ester," Chemical Abstracts, 124(18): Abstract No. 24198 (Apr. 29, 1996).

Feng et al., "Nanospheres of Biodegradable Polymers: A System for Clincal Administration of an Anticancer Drug Paclitaxel (Taxol)," Ann Acad Singapore, 29:633–639 (2000).

Francis et al., "Phase I Feasibility and Pharmacologic Study of Weekly Intraperitoneal Paclitaxel: A Gynecologic Oncology Group Pilot Study," Journal of Clincal Oncology, vol. 13, No. 12:2961–2967, Dec. (1995).

Fu et al., "Studies on the Melt Copolymerization of Phosphorous–Containing Diacid and BIS (p–Carboxyphenoxy) Propand for DDS," J. Wuhan Univ. (Natural Science Edition), 43(4):467–470 (1997).

Fu et al., "Studies on the Syntheses and Drug Release Properties of Polyanhydrides Containing Phosphonoformic (or Acetic) Acid Ethyl Ester in the Main Chain," Chemical Journal of Chinese Universities, 18(10)1706–1710 (1997).

Fu et al., "Studies on the Syntheses and Properties of Phosphorus–Containing Polyanhydrides for DDS," Chemical Journal of Chinese Universities, 18(5)813–817 (1997).

Hagiwara et al., "Pharmacologic Effects of Cisplatin Microspheres on Peritoneal Carcinomatosis in Rodents," Cancer, 71(3):844–850, Feb. (1993).

Harper et al., Enhanced Efficacy of Novel Controlled Release Paclitaxel Formulation (PACLIMER Delivery System) for Local–Regional Therapy of Lung Cancer Tumor Nodules in Mice, Clinical Cancer Research 5:4242–4248 (Dec. 1999).

Jameela et al., "Antitumour Activity of Mitoxantroneloaded Chitosan Microspheres Against Ehrlich Ascites Carcinoma," J. Pharm. Pharmacol., 48:685–688 (1996).

Kadiyala et al., "Poly(phosphoesters): Synthesis, Physicochemical Characterization and Biological Repsonse," Biomedical Applications of Synthetic Biodegradable Polymers, Chapter 3: 33–57, (Jeffrey O. Hollinger ed., 1995).

Kaetsu et al., "Biodegradable Implant Composites for Local Therapy," Journal of Controlled Release, 6:249–263 (1987).

Kumagai et al., "Improvement of Intraperitoneal Chemotherapy for Rat Ovarian Cancer Using Cisplatin–Containing Microspheres," Jpn. J. Cancer Res., 87:412–417, Apr., (1996).

Langer et al., "New Methods of Drug Delivery," Science, 249(4976):1527–33 (1990).

Leong et al., "Polymeric Controlled Drug Delivery," Advanced Drug Delivery REviews, 1:199–233 (1987).

Liu et al. "Synthesis of Phosphatidyl Ethanolamine Polyphosphate Liposomal Materials," Chemical Journal of Chinese Universities 18 (9):1556–1559 (1997).

Lo, Hungnan, "Synthesis of Biodegradable Polymers and Porous Grafts for Orthopedic Applications," Thesis, Johns Hopkins University, Jan. 27, 1995.

Mao et al., Biodegradable Polymers: Poly(Phosphoesters, Encyclopedia of Controlled Drug Delviery, Wiley and Sons, pp. 45–60 (1999).

Mao et al., "Deisgn of New Biodegradable Polymers Based on Chain–Extension of Oligomeric Lactides by Phosphates," Proceedings of the Topical Conference on Biomaterials Carriers for Drug Delivery and Scaffold for Tissue Engineering, Peppas, N.A. et al., eds. Los Angeles, CA, pp. 193–195 (1997).

Mao et al., "Synthesis and Biological Properties of Polymer Immunoadjuvants," Polymer Journal, 25(5):499–505 (1993).

Owusu–Ababio et al., "Efficacy of Sustained Release Ciprofloxacin Microspheres Against Device–Associated Pseudomonas Aeruginosa Biofilm Infection in a Rabbit Peritoneal Model," J. Med. Microbiol. Vo., 43:368–376 (1995).

Peo et al., "Biological Activity of Urease Formulated in Poloxamer 407 After Intraperitoneal Injection in the Rat," Journal of Pharmaceutical Sciences, vol. 81:7, Jul. (1992).

Perng et al., "A Phase I Feasibility and Pharmocokinetic Study of Intrapleural Paclitaxel in Patients with Malignant Pleural Effusions," Anti–Cancer Drugs, 8:565–573 (1997).

Perng et al., "Phase II Trial of Intrapleural Paclitaxel Injection for Non–Small–Cell Long Cancer Patients with Malignant Plural Effusions," Respiratory Medicine, 92:473–479 (1998).

Pretula et al., "High–Molecular–Weight Poly(alkylene phosphonate)s by Condensation for Dialkylphosphonates with Diols," Makromol. Chem., 119:671–680 (1990).

Rowinsky et al., "Paclitaxel Steady–State Plasma Concentration as a Determinant of Disease Outcome and Toxicity in Lung Cancer Patients Treated with Paclitaxel and Cisplatin," Clin. Cancer Res., 5(4):767–74 (1999).

Sato et al., "Pharmacokinetic Study of Taxol–Loaded Poly-(lactic–co–glycolic) Microspheres Containing Isopropyl Myristate After Targeted Delivery to the Lung in Mice," Biol. Pharm. Bull, 19(12):1596–601 (1996).

Sharma et al., "Antitumor Efficacy of Taxane Liposomes on a Human Ovarian Tumor Xenograft in Nude Athymic Mice," Journal of Pharmaceutical Sciences, vol. 84(12):1400–1404, Dec. (1995).

Sharma et al., "Novel Taxol® Formulation: Polyvinylpyrrolidone Nanoparticle–Encapsulated Taxol® for Drug Delivery in Cancer Therapy," Oncology Research, 8(7/8):281–286 (1996).

Suh et al., "Regulation of Smooth Muscle Cell Proliferation Using Paclitaxel–Loaded Poly(ethylene oxide)–poly(lactide/glycolide) Nanospheres," J. Biomed. Mater. Res., 42(2):331–8 (1998).

Walter et al., "Intratumoral Chemotherapy," Neurosurgery, 37(6):1129–1145, Dec. (1995).

Wang et al., "In vitro and in vivo evaluation of taxol release from poly(lactic–co–glycolic acid) microspheres containing isoproyl myristate and degradation of the microspheres," Journal of Controlled Release, 49:157–166 (1997).

Wang et al., "Preparation and Characterization of Poly(lactic–co–glycolic acid) Microspheres for Targeted Delivery of a Novel Anticancer Agent, Taxol," Chem. Pharm. Bull. 44(10):1935–1940 (1996).

Williams et al., "Combined intracranial iudr polymers and 125–I seeds for radiosensitization of experimental malignant glioma brachytherapy," American Society for Therapeutic Radiation and Oncology Abstract Annual Meeting 1997.

Williams et al., "Controlled Release of Radiochemical from Implantable Biodegradable Polymer Devices," Society Nuclear Medicine Abstract.

Williams et al., "Implantable Biodegradable Polymers for IUdR Radiosensitization of Experimental Human Malignant Glioma," Journal of Neuro–Oncology 32:181–192 (1997).

Williams et al., "Implantable Biodegradable Polymers for Radiosensitization of Human Glioma in Vivo," American Society for Therapeutic Radiation and Oncology: Abstract Annual Meeting 1997.

Williams et al., "Implantable Biodegradable Polymers for IUdR Radiosensitization of Human Glioma in Vivo," American Society for Therapeutic Radiation and Oncology: Abstract Annual Meeting 1997.

Williams et al., "Implantable Biodegradable Polymers for IUdR Radiosensitization of Human Malignant Glioma In Vivo," American Radium Society Abstract: Podium Presentation 1996 San Francisco.

Williams et al., "Implantable Biodegradable Polymers for IUdR Radiosensitization of Human Malignant Glioma In Vivo," American Society for Clinical Oncology Annual Meeting 1995 Poster Presentation (Abstract).

Williams et al., "Polymers for IUdR Radiosensitization of Experimental Glioblastoma," Congress of Neurological Surgeons Abstract: 1997.

Williams et al., "Polymers for IUdR Radiosensitization of Experimental Glioblastoma," Society Neuro Oncology Abstract: Post Nov. 1997 Meeting.

Winternitz et al., "Development of a Polymeric Surgical Paste Formulation for Taxol," Pharmaceutical Research, 13(3):368–375 (1996).

Zhang et al., "Development of Biodegradable Polymeric Paste Formulations for Taxol: An In Vitro and In Vivo Study," International Journal of Pharmaceutics, 137:199–208 (1996).

Zhang et al., "An Investigation of Antitumor Activity and Biodistribution of Polymeric Micellar Paclitaxel," Cancr Chemother. Pharmacol. 40:81–86 (1997).

Zhang et al., "Biodegradable Polymeric Pastes for Taxol: An In Vitro and In Vivo Study," Controlled Release Society, Inc., Program Book and Proceedings, Conference on Advances in Controlled Delivery, Aug. 19–20, 1996, pp. 135–136.

Zhao et al., "In Vitro Degradation Studies of Polilactofates–A Copolymer of Lactide and Phosphate," Proceed. Int'l. Symp. Control. Rel. Bioact. Mater. 27:652–653 (2000).

* cited by examiner

METHODS AND COMPOSITIONS FOR TREATING SOLID TUMORS

RELATED APPLICATIONS

This application is a continuation of U.S. Ser. No. 09/276,866, filed Mar. 26, 1999 now U.S. Pat. No. 6,537,585, which is hereby incorporated by this reference in its entirety.

BACKGROUND OF THE INVENTION

1. Field of the Invention

The present invention relates to methods for treating solid tumors, in particular those pertaining to the extended release of an antineoplastic agent from biodegradable compositions.

2. Description of the Prior Art

Antineoplastic agents, such as paclitaxel, have been used to treat solid tumors of various types. For example, those in the art have attempted to administer a variety of antineoplastic agents into the tumor itself ("intralesionally", also called "intratumorally") in the form of an aqueous slurry. See Luck et al., U.S. Pat. No. 4,978,332. However, such water-based compositions also require the presence of a vasoconstrictive drug to localize the action of the agent.

An opposite approach has also been taken by formulating a water immiscible, fatty acid ester matrix for intratumoral injection, e.g., of paclitaxel. See WO 95/17901 published 6 Jul. 1995 and Brown et al., U.S. Pat. No. 5,573,781. However, the controlled intratumoral release of the antineoplastic agent in a lipid carrier over a prolonged period of time, for example, at least three or four weeks, has not been disclosed.

Thus, there exists a need for a method of effecting the in vivo, controlled release of a variety of different antineoplastic agents into a solid tumor, whether they are small hydrophobic drugs, such as paclitaxel, or large and bulky biomacromolecules, such as therapeutically useful proteins. The effective release of the antineoplastic agent preferably occurs without requiring the presence of significant amounts of a physiologically acceptable fluid vehicle, such as normal saline or a water-immiscible organic solvent.

Biocompatible polymeric materials have been used in various therapeutic drug delivery and medical implant applications. If a medical implant is intended for use as a drug delivery or other controlled-release system, using a biodegradable polymeric carrier is one effective means to deliver the therapeutic agent locally and in a controlled fashion, see Langer et al., "Chemical and Physical Structures of Polymers as Carriers for Controlled Release of Bioactive Agents", *J. Macro. Science, Rev. Macro. Chem. Phys.*, C23(1), 61–126 (1983). In this way, less total drug is required, and toxic side effects can be minimized.

Polymers have been used for some time as carriers of therapeutic agents to effect a localized and sustained release. See Leong et al., "Polymeric Controlled Drug Delivery", *Advanced Drug Delivery Rev.*, 1:199–233 (1987); Langer, "New Methods of Drug Delivery", *Science*, 249:1527–33 (1990) and Chien et al., *Novel Drug Delivery Systems* (1982). Such delivery systems offer the potential of enhanced therapeutic efficacy and reduced overall toxicity. Examples of classes of synthetic polymers that have been studied as possible solid biodegradable materials include polyesters (Pitt et al., "Biodegradable Drug Delivery Systems Based on Aliphatic Polyesters: Applications to Contraceptives and Narcotic Antagonists", *Controlled Release of Bioactive Materials*, 19–44 (Richard Baker ed., 1980); poly(amino acids) and pseudo-poly(amino acids) (Pulapura et al. "Trends in the Development of Bioresorbable Polymers for Medical Applications", *J. Biomaterials Appl.*, 6:1, 216–50 (1992); polyurethanes (Bruin et al., "Biodegradable Lysine Diisocyanate-based Poly(Glycolide-co-ε Caprolactone)-Urethane Network in Artificial Skin", *Biomaterials*, 11:4, 291–95 (1990); polyorthoesters (Heller et al., "Release of Norethindrone from Poly(Ortho Esters)", *Polymer Engineering Sci.*, 21:11, 727–31 (1981); and polyanhydrides (Leong et al., "Polyanhydrides for Controlled Release of Bioactive Agents", *Biomaterials* 7:5, 364–71 (1986).

More specifically, Walter et al., *Neurosurgery*, 37:6, 1129–45 (1995) discloses the use of the polyanhydride PCPP-SA as a solid carrier for intratumoral administration. Others have used poly(lactic acid) as intratumoral solid carriers, for example, as needles for injection directly into the lesion. See Kaetsu et al., *J. Controlled Release*, 6:249–63 (1987); and Yamada et al., U.S. Pat. No. 5,304,377.

However, others have encountered problems with these materials. Paclitaxel has been encapsulated in poly(epsilon-caprolactone), but only about 25% of the drug was released over 6 weeks in in vitro assays. Dordunoo et al., "Taxol Encapsulation in Poly(epsilon-caprolactone) Microspheres", *Cancer Chemotherapy & Pharmacology*, 36:279–82 (1995). Poly(lactic-co-glycolic acid) microspheres have been used for the encapsulation of paclitaxel and exhibited a relatively constant release rate over three weeks in vitro, but these formulations were not evaluated in vivo. Wang et al., "Preparation and Characterization of Poly(lactic-co-glycolic acid) Microspheres for Targeted Delivery of a Novel Anticancer Agent, Taxol", *Chemical & Pharmaceutical Bulletin*, 44:1935–40 (1996). Paclitaxel has also been encapsulated in polyanhydride discs, but the resulting release rate has been described as too slow for clinical utility. Park et al., "Biodegradable polyanhydride Devices of Cefaxolin Sodium, Bupivacaine, and Taxol for Local Drug Delivery: Preparation and Kinetics and Mechanism of in vitro Release", *J. of Controlled Release*, 52:179–89 (1998).

Polymers having phosphate linkages, called poly(phosphates), poly(phosphonates) and poly(phosphites), are known. See Penczek et al., *Handbook of Polymer Synthesis*, Chapter 17: "Phosphorus-Containing Polymers", (Hans R. Kricheldorf ed., 1992). The respective structures of these three classes of compounds, each having a different side chain connected to the phosphorus atom, are as follows:

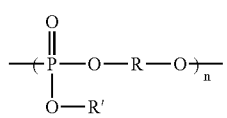

Polyphosphate

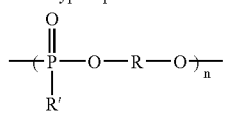

Polyphosphonate

-continued

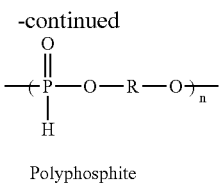

Polyphosphite

The versatility of these polymers comes from the versatility of the phosphorus atom, which is known for a multiplicity of reactions. Its bonding can involve the 3p orbitals or various 3s-3p hybrids; spd hybrids are also possible because of the accessible d orbitals. Thus, the physicochemical properties of the poly(phosphoesters) can be readily changed by varying either the R or R' group. The biodegradability of the polymer is due primarily to the physiologically labile phosphoester bond in the backbone of the polymer. By manipulating the backbone or the side chain, a wide range of biodegradation rates are attainable.

An additional feature of poly(phosphoesters) is the availability of functional side groups. Because phosphorus can be pentavalent, drug molecules or other biologically active substances can be chemically linked to the polymer. For example, drugs with —O-carboxy groups may be coupled to the phosphorus via a phosphoester bond, which is hydrolyzable. See, Leong, U.S. Pat. Nos. 5,194,581 and 5,256,765. The P-O-C group in the backbone also lowers the glass transition temperature of the polymer and, importantly, confers solubility in common organic solvents, which is desirable for easy characterization and processing.

Copending U.S. patent application Ser. No. 09/053,648 filed Apr. 2, 1998, which corresponds to PCT/US98/0681 (published Oct. 8, 1998 as WO 98/44021), discloses biodegradable terephthalate polyester-poly(phosphate) compositions. Copending patent application Ser. No. 09/053,649 filed Apr. 2, 1998, which corresponds to PCT/US98/06380 (published Oct. 8, 1998 as WO 98/44020), discloses biodegradable compositions containing polymers chain-extended by phosphoesters. Further, copending application Ser. No. 09/070,204 filed Apr. 30, 1998, which corresponds to PCT/US98/09185, discloses biodegradable compositions comprising poly(cycloaliphatic phosphoester) compounds. However, none of these disclosures suggests the specific use of biodegradable poly(phosphoester) compositions for the intratumoral treatment of solid tumors.

Thus, there remains a need for new methods and materials for the difficult problem of successfully treating tumors with a minimum of toxicity and avoiding prolonged courses of periodic re-dosing.

SUMMARY OF THE INVENTION

It has now been discovered that biodegradable polymer compositions comprising:
  (a) a poly(phosphoester) biodegradable polymer and
  (b) at least one antineoplastic agent in an amount effective to inhibit the growth of a solid tumor
are suitable for intratumoral administration to treat a mammal having a solid tumor. In a preferred embodiment, the composition comprises:
  (a) a poly(phosphoester) biodegradable polymer made by the process of reacting a phosphorodihalidate and a diol; and
  (b) at least one antineoplastic agent in an amount effective to inhibit the growth of said tumor when administered by intratumoral injection.

Alternatively, it comprises:
  (a) at least one antineoplastic agent in an amount effective to inhibit the growth of said tumor when administered by intratumoral injection; and
  (b) a poly(phosphoester) biodegradable polymer made by a process comprising the steps of:
    (1) reacting at least one heterocyclic ring compound with

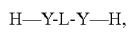

wherein H is hydrogen;
      Y is —O—, —S— or —NR$^4$—, where R$^4$ is H or alkyl; and
      L is a divalent, branched or straight chain aliphatic group having 1–20 carbon atoms to form a prepolymer;
    (2) further reacting the prepolymer with a phosphorodihalidate to form a poly(phosphoester).

The invention also comprises an article suitable for the intratumoral administration of an antineoplastic agent to a mammal having a solid tumor wherein the article comprises:
  (a) a biodegradable poly(phosphoester); and
  (b) at least one antineoplastic agent in an amount effective to inhibit the growth of said tumor when administered by intratumoral injection.

In yet another embodiment of the invention, a method is provided for treating a thoracic tumor in a mammal by the intratumoral administration of a composition comprising:
  (a) a biodegradable polymer;
  (b) at least one antineoplastic agent in an amount effective to inhibit the growth of said tumor when administered by intratumoral injection.

An alternative method for treating a solid tumor in a mammal is by the intratumoral administration of a composition comprising:
  (a) a poly(phosphoester) biodegradable polymer;
  (b) at least one antineoplastic agent in an amount effective to inhibit the growth of said tumor when administered by intratumoral injection.

The compositions of the invention can be used to deliver a wide variety of antineoplastic agents, for example, both hydrophobic drugs, such as paclitaxel, to large water-soluble macromolecules, such as proteins or DNAs, over an extended period of time without necessitating significant volumes of a delivery fluid or regular re-dosing. The methods of the invention can thus be used to significantly increase the time period over which an effective dose of the antineoplastic agent is released. Further, tumor growth is slowed to an unexpected degree. Further, the tumor suffered by the subject can be therapeutically managed with a minimum of side effects and without the unpleasantness and discomfort of a periodic series of parenteral treatments continuing to maintain a significant concentration of antineoplastic agent within the tumor.

DETAILED DESCRIPTION OF THE INVENTION

Polymeric Compositions of the Invention

Figure 1:
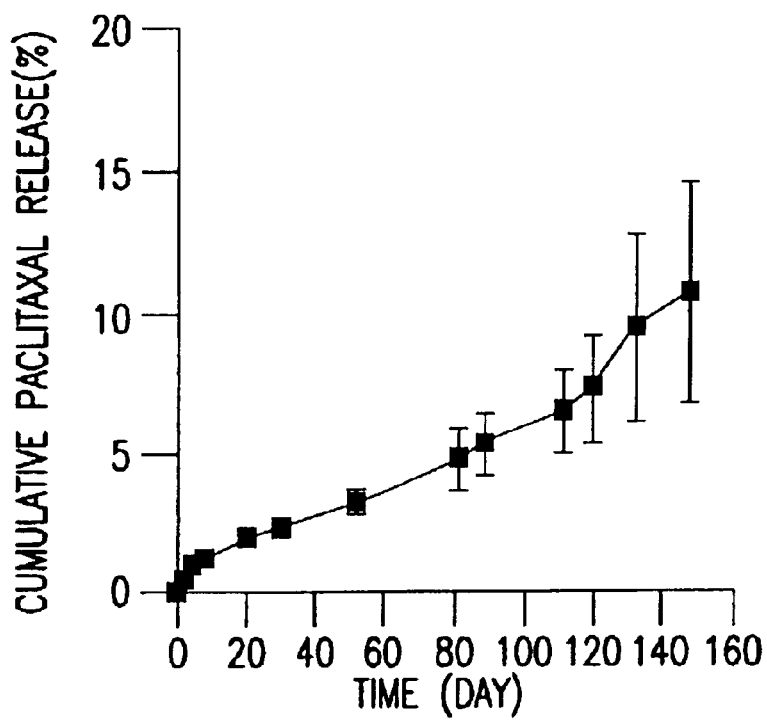
FIG. 1 shows the controlled delivery of hydrophobic small molecules, such as paclitaxel, from a film of poly(bis-hydroxyethyl terephthalate-co-ethyl phosphate/terephthalate chloride) (80:20) ["poly(BHET-EOP/TC, 80/20)"].

As used herein, the expression "mammal" refers to any mammalian subject, such as mice, rats, guinea pigs, cats, dogs, human beings, cows, horses, sheep, or other livestock.

"Cancer" comprises tissue that grows by either increased cellular proliferation and/or decreased apoptosis.

The expression "a mammal having cancer" includes, but is not limited to, subjects suffering from current symptoms of this disease and subjects who are recovering from other modes of treatment for the disease, such as surgery, chemotherapy, or other treatment.

As used herein, the term "treating" includes:
  (i) inhibiting the disease, disorder or condition, i.e., arresting its development; and
  (ii) relieving the disease, disorder or condition, i.e., causing regression of the disease, disorder and/or condition.

"Volume of tumor" means the three dimensional space occupied predominantly by a tumor in an animal as measured in cubic units.

"Intratumoral" administration means implanting a reservoir of a therapeutic agent(s) inside a tumor. Intratumoral administrations is advantageous for tumor treatment because the outer cell layers of tumors are often composed of a high percentage of necrotic cells and/or connective and support tissue which slow and/or impede the extra-tumoral vascular or parenteral delivery of therapeutic agents to the actively growing cancer cells at the center of solid tumors.

"Doubling time" means the time it takes for a population of cancer cells to double in number of cells or the time it takes for a tumor to double its volume.

"Biodegradable" means capable of being biologically decomposed. A "biodegradable" polymer can be biologically decomposed into units which may be either removed from the biological system and/or chemically incorporated into the biological system. Preferably, the inhibition of the growth of the solid tumor with the invention is measured as a delay in tumor doubling time. The use of the invention usually extends the doubling time significantly, preferably by a factor of at least two, more preferably by a factor of at least four and, most preferably, by a factor of 8–10.

Another way that the inhibition of the growth of the solid tumor with the invention is measured is as a reduction in the volume of the tumor. The use of the invention usually decreases the tumor volume significantly, preferably by at least about 10%, more preferably by at least about 30%, even more preferably by at least about 50% and, most preferably, by at least about 70%.

"Solid tumor" means a locus of tumor cells where the majority of the cells are tumor cells or tumor-associated cells.

Biodegradable polymers differ from non-biodegradable polymers in that they can be degraded during in vivo therapy. This generally involves breaking down the polymer into its monomeric subunits. In principle, the ultimate hydrolytic breakdown products of the polymer used in the invention are a diol, an aliphatic alcohol and phosphate. All of these degradation products are potentially non-toxic. However, the intermediate oligomeric products of the hydrolysis may have different properties. Thus, the toxicology of a biodegradable polymer intended for insertion into the body, even one synthesized from apparently innocuous monomeric structures, is typically determined after one or more toxicity analyses.

The expression "extended release", as used herein, includes, without limitation various forms of release, such as controlled release, timed release, sustained release, delayed release, long acting, and pulsatile delivery, immediate release that occurs with various rates. The ability to obtain extended release, controlled release, timed release, sustained release, delayed release, long acting, pulsatile delivery or immediate release is performed using well-known procedures and techniques available to the ordinarily skilled artisan. None of these specific techniques or procedures constitute an inventive aspect of this invention.

The invention contemplates a biodegradable polymer composition, article, and method for treating a subject having a solid tumor. Any of a wide variety of solid tumors may respond to the treatment of the invention, including but not limited to laryngeal tumors, brain tumors, and other tumors of the head and neck; colon, rectal and prostate tumors; breast and thoracic solid tumors; ovarian and uterine tumors; tumors of the esophagus, stomach, pancreas and liver; bladder and gall bladder tumors; skin tumors such as melanomas; and the like. Moreover, the tumor treated in the invention can be either primary or a secondary tumor resulting from metastasis of cancer cells elsewhere in the body to the chest.

Preferably, the tumor is a laryngeal, colon, rectal, prostate, breast, thoracic, bladder or skin tumor. More preferably, the tumor is a thoracic tumor such as, but not limited to, bronchogenic tumors, such as primary and/or metastatic lung carcinomas [both non-small cell lung cancer (NSCLC) and small cell lung cancer (SCLC)]; malignant pleural effusions; or cancers of the lung parenchyma, airways, chest wall and pleural spaces. Most preferably, however, the tumor is a lung solid tumor.

The term "aliphatic" refers to a linear, branched or cyclic alkane, alkene, or alkyne. Preferred linear or branched aliphatic groups in the poly(cycloaliphatic phosphoester) composition of the invention have from about 1 to 20 carbon atoms. Preferred cycloaliphatic groups may have one or more sites of unsaturation, i.e., double or triple bonds, but are not aromatic in nature.

As used herein, the term "aryl" refers to an unsaturated cyclic carbon compound with 4n+2π electrons. As used herein, the term "heterocyclic" refers to a saturated or unsaturated ring compound having one or more atoms other than carbon in the ring, for example, nitrogen, oxygen or sulfur. "Heteroaryl" refers to a heterocyclic compound with 4n+2 electrons.

As used herein, the term "non-interfering substituent" means a substituent that does react with the monomers; does not catalyze, terminate or otherwise interfere with the polymerization reaction; and does not react with the resulting polymer chain through intra- or inter-molecular reactions.

The biodegradable and injectable polymer composition of the invention comprises a biodegradable poly(phosphoester) polymer. The precise poly(phosphoester) polymer used in the invention can vary widely, depending on the hydrophilicity or hydrophobicity of the antineoplastic agent used in the composition, the physical characteristics desired, and the release profile desired. Examples of useful poly (phosphoesters) include poly(phosphates), poly(phosphites), or poly(phosphonates); poly(phosphoesters) modified with poly(carboxylic acids); poly(phenyl neocarboxylate phosphites) and poly(pentaerythrityl neocarboxylate phosphites) as described in Friedman U.S. Pat. No. 3,422,982; cyclic cycloalkylene phosphates and cyclic arylene phosphates as described in Vandenberg, U.S. Pat. No. 3,655,586; substituted ethane diphosphonates as described in Kerst, U.S. Pat. No. 3,664,975; polyhydroxychloropropyl phosphate-phosphates, as described in Cohen et al., U.S. Pat. No. 3,664,974; diphosphinic acid esters as described in Herwig et al., U.S. Pat. No. 3,875,263; poly (phenylphosphonates), as described by Desitter et al., U.S. Pat. No. 3,927,231; poly(terephthalate phosphonates), as described by Reader, U.S. Pat. No. 3,932,566; polyamidocarboxylic acids (also called polyamic acids), as described by Meyer et al., U.S. Pat. No. 3,981,847; dimethyl pentaerythritol diphosphites, alkyl alkylene phosphites, 1,3,2-dioxaphosphorinanes, aryl alkylene phosphonites, and 1,3,2-oxa-aza-phospholanes, as described by Hechenbleikner, U.S. Pat. No. 4,082,897; linear saturated polyesters of phosphoric acid and halogenated diols, as described by Login et al. in U.S. Pat. Nos. 4,259,222, 4,315,847 and 4,315,969; polyester phosphonates based on aromatic dicarboxylic acids and aromatic dihydroxy compounds, as described by Schmidt et al., U.S. Pat. Nos. 4,328,174 and 4,374,971; polyarylene esters containing phosphorus, as described by Besecke et al., U.S. Pat. Nos. 4,463,159 and 4,472,570; polyphosphates produced from indan-5-ols and triphenylphosphate, as described in Serini et al., U.S. Pat. Nos. 4,482,693 and 4,491,656; poly(phosphoester-urethanes) as described by Leong in U.S. Pat. No. 5,176,907; poly(phosphoesters) prepared from such compounds as bis-phenol A, as described by Leong in U.S. Pat. Nos. 5,194,581 and 5,256,765; and the like, the disclosures of which are hereby incorporated by reference.

Particularly preferred poly(phosphoesters), however, include those described in copending U.S. patent application Ser. No. 09/053,648 filed Apr. 2, 1998; Ser. No. 09/053,649 filed Apr. 2, 1998; and Ser. No. 09/070,204 filed Apr. 30, 1998, which correspond respectively to the following publications: PCT/US98/0681 (published Oct. 8, 1998 as WO 98/44021), PCT/US98/06380 (published Oct. 8, 1998 as WO 98/44020) and PCT/US98/09185, the disclosures of which are all hereby incorporated by reference.

Preferably, however, the poly(phosphoester) has the recurring monomeric units shown in formula I:

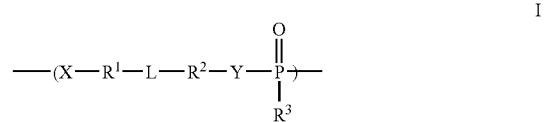

wherein X is —O— or —NR$^4$—, where R$^4$ is H or alkyl, such as methyl, ethyl, 1,2-dimethylethyl, n-propyl, isopropyl, 2-methylpropyl, 2,2-dimethylpropyl or tert-butyl, n-pentyl, tert-pentyl, n-hexyl, n-heptyl and the like.

The group Y in formula I is —O— or —NR$^4$—, where R$^4$ is as defined above.

Each of R$^1$ and R$^2$ can be any divalent organic moiety, which may be either unsubstituted or substituted with one or more non-interfering substituents, so long as the moiety and its substituents do not interfere undesirably with the polymerization, copolymerization, or biodegradation reactions of the polymer. Specifically, each of R$^1$ and R$^2$ can be a branched or straight chain aliphatic group, preferably having about 1–20 carbon atoms. For example, R$^1$ and R$^2$ can be alkylene, such as methylene, ethylene, 1-methylethylene, 1,2-dimethylethylene, n-propylene, isopropylene, 2-methylpropylene, 2,2'-dimethylpropylene or tert-butylene, n-pentylene, tert-pentylene, n-hexylene, n-heptylene, n-octylene, n-nonylene, n-decylene, n-undecylene, n-dodecylene, and the like.

R$^1$ and R$^2$ can also be alkenylene, such as ethenylene, propenylene, 2-vinylpropenylene, n-butenylene, 3-ethenylbutylene, n-pentenylene, 4-(3-propenyl)hexylene, n-octenylene, 1-(4-butenyl)-3-methyldecylene, dodecenylene, 2-(3-propenyl)dodecylene, hexadecenylene, and the like. R$^1$ and R$^2$ can also be alkynylene, such as ethynylene, propynylene, 3-(2-ethynyl)pentylene, n-hexynylene, octadecenylene, 2-(2-propynyl)decylene, and the like.

R$^1$ and R$^2$ can also be an aliphatic group, such as an alkylene, alkenylene or alkynylene group, substituted with a non-interfering substituent, for example, a hydroxy, halogen or nitrogen group. Examples of such groups include, but are not limited to, 2-chloro-n-decylene, 1-hydroxy-3-ethenylbutylene, 2-propyl-6-nitro-10-dodecynylene and the like.

Further, R$^1$ and R$^2$ can be a cycloaliphatic group, such as cyclopentylene, 2-methylcyclopentylene, cyclohexylene, cyclohexenylene and the like. Each of R$^1$ and R$^2$ can also be a divalent aromatic group, such as phenylene, benzylene, naphthalene, phenanthrenylene, and the like, or a divalent aromatic group substituted with a non-interfering substituent. Further each of R$^1$ and R$^2$ can be a divalent heterocyclic group, such as pyrrolylene, furanylene, thiophenylene, alkylene-pyrrolylene-alkylene, pyridylene, pyridinylene, pyrimidinylene and the like, or may be any of these substituted with a non-interfering substituent.

Preferably, $R^1$ and $R^2$ have from about 1–20 carbon atoms and are an alkylene group, a cycloaliphatic group, a phenylene group, or a divalent group having the formula:

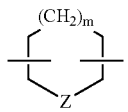

wherein Z is oxygen, nitrogen, or sulfur, and m is 1 to 3. More preferably, each of $R^1$ and $R^2$ is a branched or straight chain alkylene group having from 1 to 7 carbon atoms. Most preferably, each of $R^1$ and $R^2$ is a methylene, ethylene group, n-propylene, 2-methylpropylene, or a 2,2'-dimethylpropylene group.

In one embodiment of the invention, either $R^1$, $R^2$ or both $R^1$ and $R^2$, can be an antineoplastic agent in a form capable of being released in a physiological environment. When the antineoplastic agent part of the poly(phosphoester) backbone in this way, it is released as the polymeric matrix formed by the composition of the invention degrades.

L in the polymer composition of the invention can be any divalent, branched or straight chain aliphatic group having 1–20 carbon atom, a cycloaliphatic group, or a group having the formula:

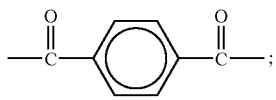

When L is a branched or straight chain alkylene group, it is preferably an alkylene group having from 1 to 7 carbon atoms, such as 2-methylmethylene or ethylene. When L is a cycloaliphatic group, it may be any divalent cycloaliphatic group so long as it does not interfere with the polymerization or biodegradation reactions of the polymer of the composition. Specific examples of useful unsubstituted and substituted cycloaliphatic L groups, include cycloalkylene groups such as cyclopentylene, 2-methylcyclopentylene, cyclohexylene, 2-chlorocyclohexylene, and the like; cycloalkenylene groups, such as cyclohexenylene; and cycloalkylene groups having fused or bridged additional ring structures on one or more sides, such as tetralinylene, decalinylene, and norpinanylene; or the like.

$R^3$ in the polymer composition of the invention is selected from the group consisting of H, alkyl, alkoxy, aryl, aryloxy, heterocyclic and heterocycloxy residues.

When $R^3$ is alkyl or alkoxy, it preferably contains about 1 to about 20 carbon atoms, even more preferably about 1 to about 15 carbon atoms and, most preferably about 1–7 carbon atoms. Examples of such groups include methyl, methoxy, ethyl, ethoxy, n-propyl, isopropoxy, n-butoxy, t-butyl, —$C_8H_{17}$; alkyl substituted with a non-interfering substituent, such as halogen, alkoxy or nitro; alkyl conjugated to a biologically active substance to form a pendant drug delivery system; and the like.

When $R^3$ is aryl or the corresponding aryloxy group, it typically contains from about 5 to about 14 carbon atoms, preferably about 5 to 12 carbon atoms and, optionally, can contain one or more rings that are fused to each other. Examples of particularly suitable aromatic groups include phenyl, phenoxy, naphthyl, anthracenyl, phenanthrenyl and the like.

When $R^3$ is heterocyclic or heterocycloxy, it typically contains from about 5 to 14 ring atoms, preferably from about 5 to 12 ring atoms, and one or more heteroatoms.

Examples of suitable heterocyclic groups include furan, thiophene, pyrrole, isopyrrole, 3-isopyrrole, pyrazole, 2-isoimidazole, 1,2,3-triazole, 1,2,4-triazole, oxazole, thiazole, isothiazole, 1,2,3-oxadiazole, 1,2,4-oxadiazole, 1,2,5-oxadiazole, 1,3,4-oxadiazole, 1,2,3,4-oxatriazole, 1,2,3,5-oxatriazole, 1,2,3-dioxazole, 1,2,4-dioxazole, 1,3,2-dioxazole, 1,3,4-dioxazole, 1,2,5-oxatriazole, 1,3-oxathiole, 1,2-pyran, 1,4-pyran, 1,2-pyrone, 1,4-pyrone, 1,2-dioxin, 1,3-dioxin, pyridine, N-alkyl pyridinium, pyridazine, pyrimidine, pyrazine, 1,3,5-triazine, 1,2,4-triazine, 1,2,3-triazine, 1,2,4-oxazine, 1,3,2-oxazine, 1,3,5-oxazine, 1,4-oxazine, o-isoxazine, p-isoxazine, 1,2,5-oxathiazine, 1,2,6-oxathiazine, 1,4,2-oxadiazine, 1,3,5,2-oxadiazine, azepine, oxepin, thiepin, 1,2,4-diazepine, indene, isoindene, benzofuran, isobenzofuran, thionaphthene, isothionaphthene, indole, indolenine, 2-isobenzazole, 1,4-pyrindine, pyrando[3,4-b]-pyrrole, isoindazole, indoxazine, benzoxazole, anthranil, 1,2-benzopyran, 1,2-benzopyrone, 1,4-benzopyrone, 2,1-benzopyrone, 2,3-benzopyrone, quinoline, isoquinoline, 12,-benzodiazine, 1,3-benzodiazine, naphthpyridine, pyrido[3,4-b]-pyridine, pyrido[3,2-b]-pyridine, pyrido[4,3-b]pyridine, 1,3,2-benzoxazine, 1,4,2-benzoxazine, 2,3,1-benzoxazine, 3,1,4-benzoxazine, 1,2-benzisoxazine, 1,4-benzisoxazine, carbazole, xanthrene, acridine, purine, and the like. Preferably, when $R^3$ is heterocyclic or heterocycloxy, it is selected from the group consisting of furan, pyridine, N-alkylpyridine, 1,2,3- and 1,2,4-triazoles, indene, anthracene and purine rings.

In a particularly preferred embodiment, $R^3$ is an alkyl group, an alkoxy group, a phenyl group, a phenoxy group, or a heterocycloxy group and, even more preferably, an alkoxy group having from 1 to 10 carbon atoms. Most preferably, $R^3$ is an ethoxy or hexyloxy group.

Alternatively, the side chain $R^3$ can be the antineoplastic agent or some other biologically active substance pendently attached to the polymer backbone, for example by ionic or covalent bonding. In this pendant system, the antineoplastic agent or other biologically active substance is released as the bond connecting $R^3$ with the phosphorous atom is cleaved under physiological conditions.

The number of recurring monomeric units can vary greatly depending on the biodegradability and the release characteristics desired in the polymer, but typically varies between about 5 and 1,000. Preferably, the number of recurring units is from about 5 to about 500 and, most preferably, is from about 5 to about 400.

When used in accordance with the method of the invention, the polymer composition provides extended release of the antineoplastic agent into the solid tumor of a subject having one or more of such tumors, preferably for a period greater than about one day. Even more preferably, the release profile extends over a time of at least about 15 days, still more preferably at least about 30 days, for example, from at least about four weeks to a year.

More preferably, however, the poly(phosphoester) polymer of the invention is a phosphoester co-ester.

In one embodiment, the biodegradable poly (phosphoester) of the invention has a molecular weight between about 2 and 500 KDaltons and comprises monomeric units represented by formulas II and III:

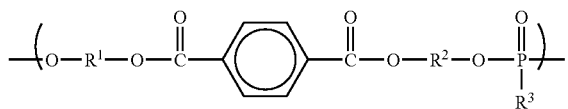

II

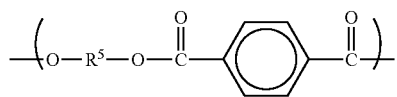

III wherein each of $R^1$, $R^2$ and $R^5$ is a divalent organic moiety; and $R^3$ is selected from the group consisting of alkoxy, aryloxy and heterocycloxy.

Even more preferably, $R^1$, $R^2$ and $R^5$ are each independently an alkylene group having from 1 to 7 carbons atoms; and $R^3$ is an alkoxy group having from 1 to 7 carbon atoms. Most preferably, $R^1$, $R^2$ and $R^5$ are each independently selected from the group consisting of ethylene, n-propylene, 2-methylpropylene and 2,2-dimethyl-propylene; and $R^3$ is ethoxy.

In another embodiment, the polymer composition of the invention comprises a biodegradable poly(phosphoester) has a molecular weight between about 2 and 500 KDaltons and comprising monomeric units represented by formulas IV, V, VI and VII:

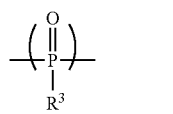

IV

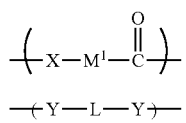

V

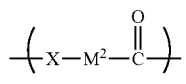

VI

VII wherein X is —O— or —NR$^4$—;
Y is —O—, —S— or —NR$^4$—;
$R^4$ is H or alkyl;
$M^1$ and $M^2$ are each independently (1) a branched or straight chain aliphatic group having from 1–20 carbon atoms; or (2) a branched or straight chain, oxy-, carboxy- or amino-aliphatic group having from 1–20 carbon atoms;
L is a divalent, branched or straight chain aliphatic group having 1–20 carbon atom; and
$R^3$ is selected from the group consisting of H, alkyl, alkoxy, aryl, aryloxy, heterocyclic or heterocycloxy.

In formulas IV–VII, the molar ratios of the various monomers to each other can vary greatly depending on the biodegradability and the release characteristics desired in the polymer but, typically, is about 1:10:1:10, respectively.

In formulas V and VII, each of $M^1$ and $M^2$ is preferably a branched or straight chain alkylene or alkoxylene group, more preferably having from 1–20 carbon atoms. Even more preferably, at least one of $M^1$ and $M^2$ is an alkylene or alkoxylene group having a formula selected from the group consisting of —(CH$_2$)$_a$—, —(CH$_2$)$_a$—O—, and —(CH$_2$)$_a$—O—(CH$_2$)$_b$—, wherein each of a and b is 1–7.

When either $M^1$ or $M^2$ is a branched or straight chain, carboxy-aliphatic group having from 1–20 carbon atoms, it can also be, for example, a divalent carboxylic acid ester such as the divalent radical corresponding to methyl formate, methyl acetate, ethyl acetate, n-propyl acetate, isopropyl acetate, n-butyl acetate, ethyl propionate, allyl propionate, t-butyl acrylate, n-butyl butyrate, vinyl chloroacetate, 2-methoxycarbonyl cyclohexanone, 2-acetoxycyclohexanone, and the like. When $M^1$ or $M^2$ is a branched or straight chain, carboxy-aliphatic group, it preferably has the formula —CHR'—CO—O—CHR"—, wherein R' and R" are each independently H, alkyl, alkoxy, aryl, aryloxy, heterocyclic or heterocycloxy.

When either $M^1$ or $M^2$ is a branched or straight chain, amino-aliphatic group having from 1–20 carbon atoms, it can be a divalent amine such as —CH$_2$NH—, —(CH$_2$)$_2$N—, —CH$_2$(C$_2$H$_5$)N—, -n-C$_4$H$_9$—NH—, -t-C$_4$H$_9$—NH—, —CH$_2$(C$_3$H$_6$)N—, —C$_2$H$_5$(C$_3$H$_6$)N—, —CH$_2$(C$_8$H$_{17}$)N—, and the like. When $M^1$ or $M^2$ is a branched or straight chain, amino-aliphatic group, it preferably has the formula —(CH$_2$)$_a$—NR' where R' is H or lower alkyl, and "a" is from 1 to 7.

Preferably, $M^1$ and/or $M^2$ is an alkylene group having the formula —O—(CH$_2$)$_a$— where a is 1 to 7 and, most preferably, is a divalent ethylene group. In another particularly preferred embodiment, $M^1$ and $M^2$ are n-pentylene and the divalent radical corresponding to methyl acetate respectively.

Preferably, $R^3$ in formulas IV–VII is an alkoxy group; X and Y are each oxygen; and $M^1$, $M^2$ and L are each independently a branched or straight chain alkylene group having from 1 to 7 carbon atoms. Still more preferably, $R^3$ is an alkoxy group having from 1 to 7 carbon atoms; L is alkylene; and $M^1$ and $M^2$ are each independently an alkylene group having from 1 to 3 carbon atoms.

In preferred polymers of formula VIII and IX:

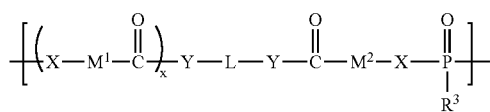

VIII

-continued

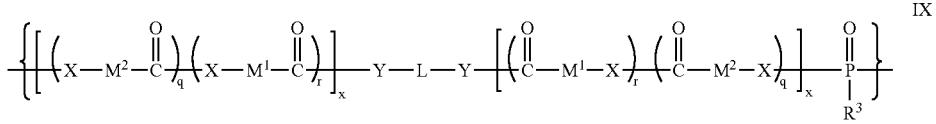

wherein X, Y and R³ are as defined above;

M¹ and M² are each independently (1) a branched or straight chain aliphatic group having from about 1–20 carbon atoms, even more preferably from about 1–7 carbon atoms; or (2) a branched or straight chain, oxy-, carboxy- or amino-aliphatic group having from about 1–20 carbon atoms, such as ethoxylene, 2-methylethoxylene, propoxylene, butoxylene, pentoxylene, dodecyloxylene, hexadecyloxylene, and the like;

L is a divalent, branched or straight chain aliphatic group having 1–20 carbon atoms;

each of x and y is about 1 to 1,000;

the molar ratio of x:y can vary greatly depending on the biodegradability and the release characteristics desired in the polymer but, typically, is about 1;

the molar ratio q:r can also vary greatly depending on the biodegradability and the release characteristics desired in the polymer, but typically varies between about 1:200 and 200:1, preferably between about 1:150 to about 150:1 and, most preferably, between about 1:99 and 99:1.

In yet another preferred embodiment, the polymer composition of the invention comprises a biodegradable poly(phosphoester) having a molecular weight between about 2 and 500 KDaltons and comprising monomeric units represented by formula X:

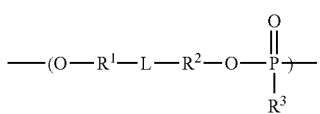

wherein each of R¹ and R² is independently straight or branched aliphatic, either unsubstituted or substituted with one or more non-interfering substituents; and L is a divalent cycloaliphatic group; and R³ is selected from the group consisting of H, alkyl, alkoxy, aryl, aryloxy, heterocyclic or heterocycloxy.

Preferably, each of R¹ and R² is a methylene group; R³ is an alkoxy group having from 1 to 6 carbon atoms; and L is cyclohexylene.

Most preferably, the biodegradable composition is suitable for intratumoral administration to treat a mammal having a thoracic solid tumor, and the composition comprises:

(a) paclitaxel and (b) a biodegradable polymer having a molecular weight between about 2 and 500 KDaltons and comprising monomeric units shown in formula XI:

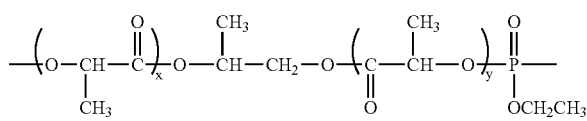

wherein the delay in tumor doubling time is extended by a factor of at least two. Typically, the molar ratio of x:y in formula XI is about 1:1.

The molecular weight of the polymer used in the composition of the invention can vary widely, depending on whether a rigid solid state (higher molecular weights) is desirable, or whether a flowable or flexible state (lower molecular weights) is desired. Molecular weights are determined by standard techniques well known to the ordinary skilled artisan, such as GPC and light scattering. Generally, however, weight-average molecular weights (Mw) typically vary from about 2,000 to about 500,000 daltons, preferably from about 5,000 to about 200,000 daltons and, even more preferably, from about 5,000 to 100,000 daltons.

One method to determine molecular weight is by combined gel permeation chromatography ("GPC") and light scattering, e.g., mixed bed columns, CH₂Cl₂ solvent, refractive index detector, and light scattering detector. Off-line dn/dc measurements are typically used.

The biodegradable polymer used in the invention is preferably sufficiently pure to be biocompatible itself and remains biocompatible upon biodegradation. By "biocompatible", it is meant that the biodegradation products or the polymer itself are non-toxic and result in only minimal tissue irritation when injected or placed into intimate contact with vasculated tissues. The requirement for biocompatibility is more easily accomplished because the presence of an organic solvent is not required in the polymer composition of the invention.

However, the polymer used in the invention is preferably soluble in one or more common organic solvents for ease of synthesis, purification and handling. Common organic solvents include such solvents as ethanol, chloroform, dichloromethane (dimethylene chloride), acetone, ethyl acetate, DMAC, N-methyl pyrrolidone, dimethylformamide, and dimethylsulfoxide. The polymer is preferably soluble in at least one of the above solvents. The biodegradable polymer of the invention can also comprise additional biocompatible monomeric units so long as they do not interfere with the biodegradable characteristics and the desirable flow characteristics of the invention. Such additional monomeric units may offer even greater flexibility in designing the precise release profile desired for targeted drug delivery or the precise rate of biodegradability desired for other applications. When such additional monomeric units are used, however, they should be used in small enough amounts to insure the production of a biodegradable copolymer having the desired physical characteristics, such as rigidity, viscosity, flowability, flexibility or a particular morphology.

Examples of such additional biocompatible monomers include the recurring units found in other poly (phosphoesters), poly(esters), poly(lactides), poly (glycolides), poly(caprolactones), poly(anhydrides), poly (amides), poly(urethanes), poly(esteramides), poly (orthoesters), poly(dioxanones), poly(acetals), poly(ketals), poly(carbonates), poly(imino-carbonates), poly (orthocarbonates), poly(phosphazenes), poly (hydroxybutyrates), poly(hydroxyvalerates), poly(alkylene oxalates), poly(alkylene succinates), poly(malic acids), poly (amino acids), poly(vinylpyrrolidone), poly(ethylene glycol), poly(hydroxycellulose), chitin, chitosan, and copolymers, terpolymers, or combinations or mixtures of the above materials. Preferably, however, a poly(phosphoester) is the major component of the composition used with the invention.

When additional monomeric units are used, those which have a lower degree of crystallization and are more hydrophobic are preferred. Especially preferred recurring units with the desired physical characteristics are those derived from poly(lactides), poly(caprolactones), and copolymers of these with glycolide.

Synthesis of Poly(Phosphoester) Polymers

The most common general reaction in preparing poly (phosphates) is a dehydrochlorination between a phosphorodihalidate, such as phosphorodichloridate, and a diol according to the following equation:

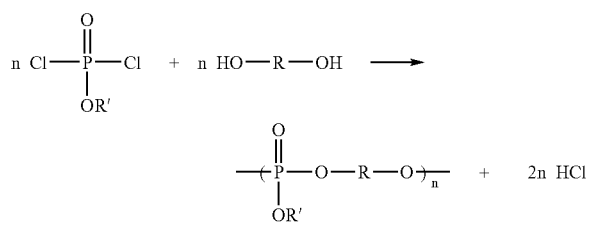

Most poly(phosphonates) are also obtained by condensation between appropriately substituted dichlorides and diols.

Poly(phosphites) have been prepared from glycols in a two-step condensation reaction. A 20% molar excess of a dimethylphosphite is used to react with the glycol, followed by the removal of the methoxyphosphonyl end groups in the oligomers by high temperature and under a vacuum.

An advantage of melt polycondensation is that it avoids the use of solvents and large amounts of other additives, thus making purification more straightforward. It can also provide polymers of reasonably high molecular weight. Somewhat rigorous conditions, however, are often required and can lead to chain acidolysis (or hydrolysis if water is present). Unwanted, thermally-induced side reactions, such as crosslinking reactions, can also occur if the polymer backbone is susceptible to hydrogen atom abstraction or oxidation with subsequent macroradical recombination.

To minimize these side reactions, the polymerization can also be carried out in solution. Solution polycondensation requires that both the prepolymer and the phosphorus component be soluble in a common solvent. Typically, a chlorinated organic solvent is used, such as chloroform, dichloromethane, or dichloroethane.

A solution polymerization is preferably run in the presence of equimolar amounts of the reactants and a stoichiometric amount of an acid acceptor, usually a tertiary amine such as pyridine or triethylamine. Because overall milder reaction conditions can be used, side reactions are minimized, and more sensitive functional groups can be incorporated into the polymer.

Interfacial polycondensation can be used when high reaction rates are desired. The mild conditions used minimize side reactions, and there is no need for stoichiometric equivalence between the diol and dichloridate starting materials as in solution methods. The yield and molecular weight of the resulting polymer after interfacial polycondensation are affected by reaction time, molar ratio of the monomers, volume ratio of the immiscible solvents, the type of acid acceptor, and the type and concentration of the phase transfer catalyst.

The purpose of the polymerization reaction is to form a polymer comprising (i) divalent organic recurring units and (ii) phosphoester recurring units. The result can be a homopolymer, a relatively homogeneous copolymer, or a block copolymer. Any one of these three embodiments is well-suited for use as a controlled release medium.

While the process may be in bulk, in solution, by interfacial polycondensation, or any other convenient method of polymerization, preferably, the process takes place under solution conditions. Particularly useful solvents include methylene chloride, chloroform, tetrahydrofuran, dimethyl formamide, dimethyl sulfoxide, toluene, or any of a wide variety of other inert organic solvents.

Particularly when solution polymerization reaction is used, an acid acceptor is advantageously present during the polymerization reaction. A particularly suitable class of acid acceptor comprises tertiary amines, such as pyridine, trimethylamine, triethylamine, substituted anilines and substituted aminopyridines. The most preferred acid acceptor is the substituted aminopyridine 4-dimethylaminopyridine ("DMAP").

In a particularly preferred embodiment of the invention, for example, the biodegradable polymer of formula VIII or IX is made by a process comprising the steps of:

(a) reacting at least one heterocyclic ring compound having formula XII, XIII or XIV:

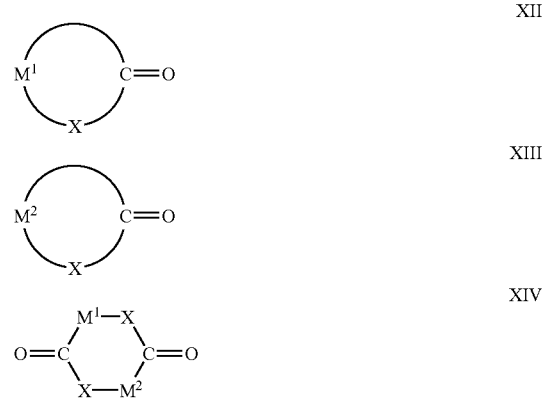

wherein $M^1$, $M^2$ and X are as defined above, with an initiator having the formula:

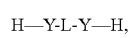

H—Y-L-Y—H, wherein Y and L are as defined as above, to form a prepolymer of formula XV or XVI, shown below:

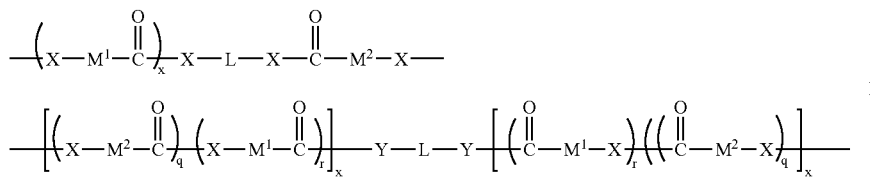

wherein X, M$^1$, M$^2$, Y, L, R, x, y, q and r are as defined above; and (b) further reacting the prepolymer with a phosphorodihalidate of formula XVII:

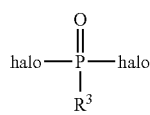

XVII where "halo" is Br, Cl or I; and R$^3$ is as defined above, to form a polymer of formula VIII or IX.

The function of the first reaction step (a) is to use the initiator to open the ring of the heterocyclic ring compound of formula XII, XIII or XIV. Examples of useful heterocyclic compounds of formula XII, XIII or XIV include lactones, lactams, amino acid anhydrides such as glycine anhydride, cycloalkylene carbonates, dioxanones, glycolids, lactides and the like.

When the compound of the invention has formula VIII, only one heterocyclic ring compound of formula XII, which contains M$^1$, may be used to prepare the prepolymer in step (a). When the compound of the invention has formula IX, then a combination of a heterocyclic compound of formula XII, which contains M$^1$, and a heterocyclic compound of formula XIII, which contains M$^2$ may be used in step (a). Alternatively, when the compound of the invention has formula IX, a single heterocyclic compound of formula XIV, which contains both M$^1$ and M$^2$ can be used in step (a).

Examples of suitable initiators include a wide variety of compounds having at least two active hydrogens (H—Y-L-Y—H) where H is hydrogen, L is a linking group and is defined above, and Y can be —O—, —S— or —NR$^4$, where R$^4$ is as defined above. The linking group L is can be a straight chain group, e.g., alkylene, but it may also be substituted with one or more additional active-hydrogen-containing groups. For example, L may be a straight chain alkylene group substituted with one or more additional alkyl groups, each bearing a activated hydrogen moiety, such as —OH, —SH, or NH$_2$. In this way, various branched polymers can be prepared using the branched active hydrogen initiators to design the resulting polymer such that it has the desired properties. However, when branched polymers are reacted with acid chlorides, cross-linked polymers will result.

The reaction step (a) can take place at widely varying temperatures, the molecular weight desired, the susceptibility of the reactants to form side reactions, and the presence of a catalyst. Preferably, however, the reaction step (a) takes place at a temperature from about 110° to about +235° C. for melt conditions. Somewhat lower temperatures may be possible with the use of either a cationic or anionic catalyst.

While the reaction step (a) may be in bulk, in solution, by interfacial polycondensation, or any other convenient method of polymerization, preferably, the reaction step (a) takes place under melt conditions.

Examples of particularly useful prepolymers of formula XVI include:

(i) OH-terminated copolymer derived from lactide and glycolide:

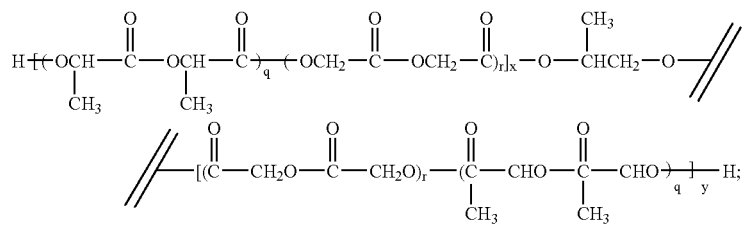

(ii) OH-terminated copolymer derived from lactide and caprolactone:

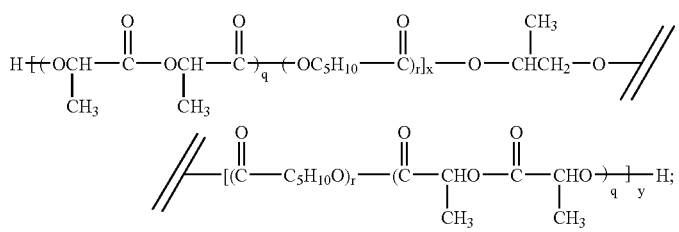

and (iii) OH-terminated copolymer derived from glycolide and caprolactone:

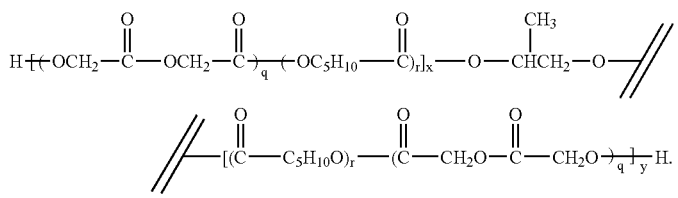

The purpose of the polymerization of step (b) is to form a polymer comprising (i) the prepolymer produced as a result of step (a) and (ii) interconnecting phosphorylated units. The result can be a block or random copolymer that is particularly well-suited to use as a controlled release medium.

The polymerization step (b) of the invention usually takes place at a lower temperature than the temperature of step (a), but also may vary widely, depending upon the type of polymerization reaction used, the presence of one or more catalysts, the molecular weight desired, and the susceptibility of the reactants to undesirable side reaction. When melt conditions are used, the temperature may vary from about 0–150° C. However, when the polymerization step (b) is carried out in a solution polymerization reaction, it typically takes place at a temperature between about –40 and 100° C.

Antineoplastic Agent

Generally speaking, the antineoplastic agents of the invention can vary widely depending upon the pharmacological strategy selected for slowing the growth, or actually reducing the size, of the solid tumor. The antineoplastic agent may be described as a single entity or a combination of entities. The compositions, articles and methods are designed to be used with antineoplastic agents having high water-solubility, as well as those having low water-solubility, to produce a delivery system that has controlled release rates.

The term antineoplastic agent includes, without limitation, platinum-based agents, such as carboplatin and cisplatin; nitrogen mustard alkylating agents; nitrosourea alkylating agents, such as carmustine (BCNU) and other alkylating agents; antimetabolites, such as methotrexate; purine analog antimetabolites; pyrimidine analog antimetabolites, such as fluorouracil (5-FU) and gemcitabine; hormonal antineoplastics, such as goserelin, leuprolide, and tamoxifen; natural antineoplastics, such as taxanes (e.g., docetaxel and paclitaxel), aldesleukin, interleukin-2, etoposide (VP-16), interferon alfa, and tretinoin (ATRA); antibiotic natural antineoplastics, such as bleomycin, dactinomycin, daunorubicin, doxorubicin, and mitomycin; and vinca alkaloid natural antineoplastics, such as vinblastine and vincristine.

Preferably, the antineoplastic agent is selected from the group consisting of the taxanes and other antitubullins including, but not limited to, paclitaxel, docetaxel and other synthetic taxanes. The taxanes are complex esters consisting of a 15-member taxane ring system linked to a four-member oxetan ring. In paclitaxel and docetaxel, for example, the taxane ring is linked to as ester side chain attached at the c-13 position of the ring, which is thought to be important for antitumor activity. The structures of paclitaxel and docetaxel differ in substitutions at the C-10 taxane ring position and on the ester side chain attached at C-13. Most preferably, the antineoplastic agent is paclitaxel, the structure of which is shown below with docetaxel and the precursor taxane 10-deacetyl-baccatin III.

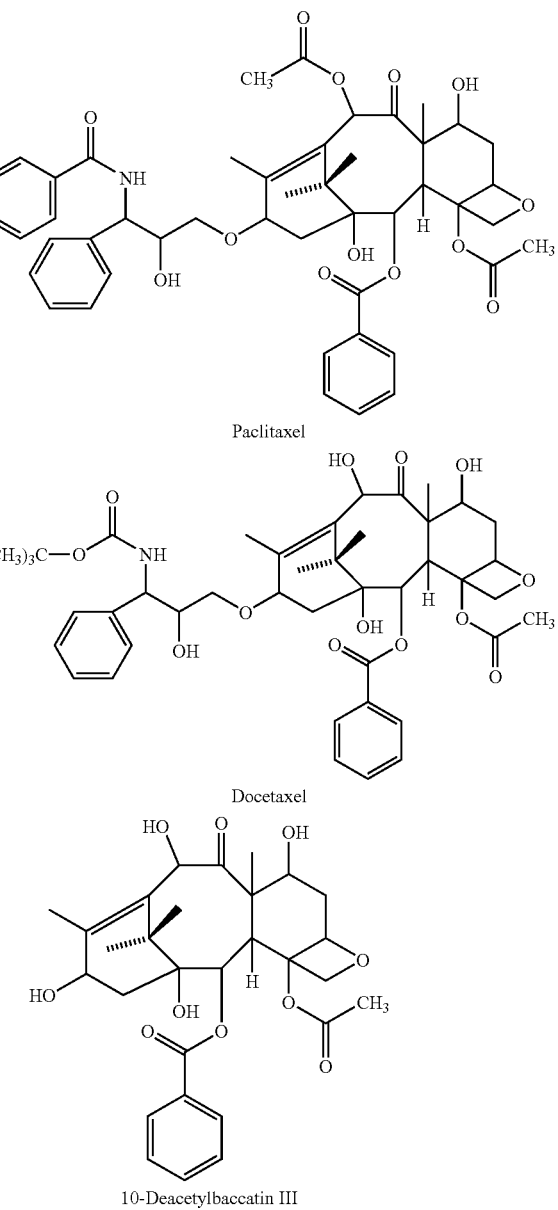

The compound 10-deacetyl-baccatin III can be used to make a wide variety of related compounds that also exhibit antineoplastic effects.

Further, the following additional drugs may also be used in combination with the antineoplastic agent, even if not considered antineoplastic agents themselves: dactinomycin; daunorubicin HCl; docetaxel; doxorubicin HCl; epoetin alfa; etoposide (VP-16); ganciclovir sodium; gentamicin sulfate; interferon alfa; leuprolide acetate; meperidine HCl; methadone HCl; ranitidine HCl; vinblastin sulfate; and zidovudine (AZT). For example, fluorouracil has recently been formulated in conjunction with epinephrine and bovine collagen to form a particularly effective combination.

Still further, the following listing of amino acids, peptides, polypeptides, proteins, polysaccharides, and other large molecules may also be used: interleukins 1 through 18, including mutants and analogues; interferons or cytokines, such as interferons α, β, and γ; hormones, such as luteinizing hormone releasing hormone (LHRH) and analogues and, gonadotropin releasing hormone (GnRH); growth factors, such as transforming growth factor-β (TGF-β), fibroblast growth factor (FGF), nerve growth factor (NGF), growth hormone releasing factor (GHRF), epidermal growth factor (EGF), fibroblast growth factor homologous factor (FGFHF), hepatocyte growth factor (HGF), and insulin growth factor (IGF); tumor necrosis factor-α & β (TNF-α & β); invasion inhibiting factor-2 (IIF-2); bone morphogenetic proteins 1–7 (BMP 1–7); somatostatin; thymosin-α-1; γ-globulin; superoxide dismutase (SOD); complement factors; anti-angiogenesis factors; antigenic materials; and pro-drugs.

In a particularly preferred embodiment, the composition of the invention may comprise other biologically active substances, preferably a therapeutic drug or pro-drug, for example, other chemotherapeutic agents, antibiotics, anti-virals, anti-fungals, anti-inflammatories, vasoconstrictors and anticoagulants, antigens useful for cancer vaccine applications or corresponding pro-drugs.

Various forms of the antineoplastic agents and/or other biologically active agents may be used. These include, without limitation, such forms as uncharged molecules, molecular complexes, salts, ethers, esters, amides, and the like, which are biologically activated when implanted, injected or otherwise inserted into the tumor.

Polymer Compositions

The antineoplastic agents are used in amounts that are therapeutically effective, which varies widely depending largely on the particular antineoplastic agent being used. The amount of antineoplastic agent incorporated into the composition also depends upon the desired release profile, the concentration of the agent required for a biological effect, and the length of time that the antineoplastic agent should be released for treatment.

There is no critical upper limit on the amount of antineoplastic agent incorporated except for that of an acceptable solution or dispersion viscosity to maintain the physical characteristics desired for the composition. The lower limit of the antineoplastic agent incorporated into the delivery system is dependent upon the activity of the drug and the length of time needed for treatment. Thus, the amount of the antineoplastic agent should not be so small that it fails to produce the desired physiological effect, nor so large that the antineoplastic agent is released in an uncontrollable manner.

Typically, within these limits, amounts of the antineoplastic agents from about 1% up to about 65%, and preferably from about 1% to about 30% by weight, can be incorporated into the present delivery systems. However, lesser amounts may be used to achieve efficacious levels of treatment for antineoplastic agent that are particularly potent.

In addition, the biodegradable polymer composition of the invention may also comprise blends of the polymer of the invention with other biocompatible polymers or copolymers, so long as the additional polymers or copolymers do not interfere undesirably with the biodegradable or mechanical characteristics of the composition. Preferably, biodegradable polymers of the present invention comprise more than about 50% of the blend. Blends of the polymer of the invention with such other polymers may offer even greater flexibility in designing the precise release profile desired for targeted drug delivery or the precise rate of biodegradability desired. Examples of such additional biocompatible polymers include other poly(phosphoesters), poly(esters), poly(lactides), poly(glycolides), poly(caprolactones), poly(anhydrides), poly(amides), poly(urethanes), poly(esteramides), poly(orthoesters), poly(dioxanones), poly(acetals), poly(ketals), poly(carbonates), poly(iminocarbonates), poly(orthocarbonates), poly(phosphazenes), poly(hydroxybutyrates), poly(hydroxyvalerates), poly(alkylene oxalates), poly(alkylene succinates), poly(malic acids), poly(amino acids), poly(vinylpyrrolidone), poly(ethylene glycol), poly(hydroxycellulose), chitin, chitosan, and copolymers, terpolymers, or combinations or mixtures of the above materials.

Pharmaceutically acceptable polymeric carriers may also comprise a wide range of additional materials. Without limitation, such materials may include well-known diluents, binders and adhesives, lubricants, disintegrants, colorants, bulking agents, flavorings, sweeteners, and miscellaneous materials such as buffers and adsorbents, in order to prepare a particular medicated composition. The addition of such materials is limited to those additional materials which will not interfere with the biocompatibility, biodegradability and physical state desired of the polymer compositions of the invention.

For delivery of an antineoplastic agent or some other biologically active substance, the agent or substance is added to the polymer composition. The agent or substance is either dissolved to form a homogeneous solution of reasonably constant concentration in the polymer composition, or dispersed to form a suspension or dispersion within the polymer composition at a desired level of "loading" (grams of biologically active substance per grams of total composition including the biologically active substance, usually expressed as a percentage).

While it is possible that the biodegradable polymer or the biologically active agent may be dissolved in a small quantity of a solvent that is non-toxic to more efficiently produce an amorphous, monolithic distribution or a fine dispersion of the biologically active agent in the flexible or flowable composition, it is an advantage of the invention that, in a preferred embodiment, no solvent is needed to form the desired composition.

The polymer composition of the invention may be a rigid solid article, a flexible solid article or material, or a flowable material. By "flowable" is meant the ability to assume, over time, the shape of the space containing it at body temperature. This includes, for example, liquid compositions that are capable of being sprayed into a site; injected with a manually operated syringe fitted with, for example, a 23-gauge needle; or delivered through a catheter.

Also included by the term "flowable", however, are highly viscous, "gel-like" materials at room temperature that may be delivered to the desired site by pouring, squeezing from a tube, or being injected with any one of the commercially available power injection devices that provide injection pressures greater than would be exerted by manual means alone for highly viscous, but still flowable, materials. Such flowable polymer compositions have the advantage of providing controllable and effective release of the antineoplastic agent over time, even in formulations containing large bio-macromolecules.

When the polymer used is itself flowable, the polymer composition of the invention, even when viscous, need not include a biocompatible solvent to be flowable, although trace or residual amounts of biocompatible solvents may still be present. The degree of viscosity of the polymer can be adjusted by the molecular weight of the polymer, as well as by mixing any cis- and trans-isomers of the diol in the backbone of the polymer.

The polymer composition of the invention can be administered by a variety of routes. For example, if flowable, it can be injected directly into the solid tumor being treated with a needle, such as a Turner Biopsy Needle or a Chiba Biopsy Needle. When treating a solid tumor in the lung, for example, the composition may be administered within the thorax using bronchoscope or other device capable of cannulating the bronchial tree (e.g., from Cook Catheter Company). Masses accessible via the bronchial tree may be directly injected by using one of the widely available transbronchial aspiration needles (e.g., from Milrose or Boston Scientific). The composition can also be administered within the pleural space by inserting a thoracentesis catheter or needle between the ribs into the pleural space using standard thoracentesis techniques.

The polymer composition of the invention can also be used to produce coatings for solid devices implantable within the tumor, such as needles, rods, microparticles or stents.

Implants and Delivery Systems

In its simplest form, a biodegradable polymer delivery system consists of a solution or dispersion of an antineoplastic agent in a polymer matrix having an unstable (biodegradable) bond incorporated into the polymer backbone. In a particularly preferred embodiment, a solid article comprising the composition of the invention is inserted into the solid tumor being treated by implantation, injection, or otherwise being placed within the tumor of the subject being treated, for example, during or after the surgical removal of a portion of visibly cancerous tissue.

The antineoplastic agent of the composition and the polymer may form a homogeneous matrix, for example in the form of microspheres, or the antineoplastic agent may be encapsulated in some other way within the polymer. For example, the antineoplastic agent may be first encapsulated in a microsphere and then combined with the polymer in such a way that at least a portion of the microsphere structure is maintained. Alternatively, the antineoplastic agent may be sufficiently immiscible in the polymer of the invention that it is dispersed as small droplets, rather than being dissolved, in the polymer.

As a structural medical device, the polymer compositions of the inventions provide a wide variety of physical forms having specific chemical, physical and mechanical properties suitable for insertion into the tumor being treated, in addition to being a composition that degrades in vivo into non-toxic residues. Specifically, the composition itself may be fabricated to take the shape of a needle or pin that can be manually inserted into the tumor mass.

Biodegradable drug delivery articles can be prepared in several ways. The polymer can be melt processed using conventional extrusion or injection molding techniques, or these products can be prepared by dissolving in an appropriate solvent, followed by formation of the device, and subsequent removal of the solvent by evaporation or extraction, e.g., by spray drying. By these methods, the polymers may be formed into articles of almost any size or shape desired, for example, implantable or injectable needles, rods, microspheres, or other microparticles. Typical medical articles also include coatings to be placed on other implant devices.

Once inserted, the polymer composition of the invention should remain in at least partial contact with tumorous cells and the biological fluids found within tumors, such as blood and various hormones and enzymes associated with angiogenesis, and the like. The implanted or injected composition will release the antineoplastic agent contained within its matrix within the tumor at a controlled rate until the substance is depleted, following the general rules for diffusion or dissolution from a rigid, flexible or flowable biodegradable polymeric matrix.

The method of the invention can be used to treat a solid tumor in a mammal by the intratumoral administration of a composition comprising:

(a) a biodegradable polymer; and (b) at least one antineoplastic agent in an amount effective to inhibit the growth of the tumor when administered by intratumoral injection.

While the method of the invention is available to treat a wide variety of solid tumors, as described above, it is particularly applicable to thoracic cancers, such as, but not limited to, bronchogenic tumors, such as primary and/or metastatic lung carcinomas (both NSCLC and SCLC); malignant pleural effusions; or non-thoracic cancers metastasizing to any site within the thorax.

The biodegradable polymer used in a composition to treat a thoracic tumor can comprise any biodegradable polymer, rather than being limited to poly(phosphoester) polymers. Without limitation, exemplary biodegradable polymers suitable for practicing the invention are polyanhydrides, polyesters, poly(phosphoesters), polyorthoesters, polyphosphazenes, polyesteramides, polydioxanones, polyhydroxybutyrates, polyhydroxyvalerates, polyalkylene oxalates, polyalkylene succinates, poly(malic acids), poly (amino acids) and copolymers, terpolymers and combinations and mixtures of the above, and the like. Preferably, however, the biodegradable polymer comprises a poly (phosphoester).

The following examples are illustrative of preferred embodiments of the invention and are not to be construed as limiting the invention thereto. All polymer molecular weights are weight-average molecular weights unless otherwise indicated. All percentages are based on the percent by weight of the final delivery system or formulation being prepared, unless otherwise indicated, and all totals equal 100% by weight.

EXAMPLES

Example 1

Synthesis of Copolymer Poly(BHET-EOP/TC, 80/20)

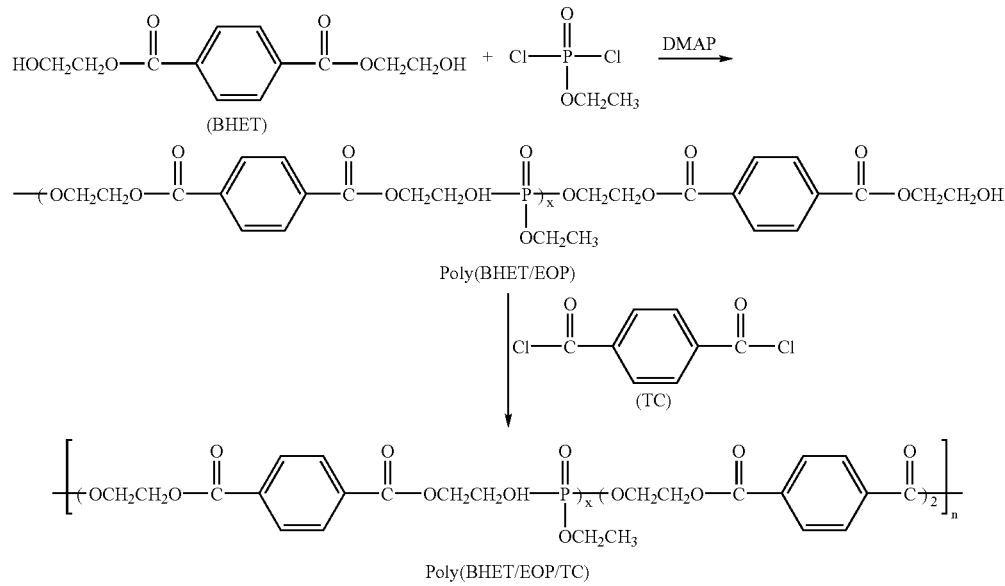

Under an argon stream, 10 g of 1,4-bis(hydroxyethyl) terephthalate (BHET), 9.61 g of 4-dimethylaminopyridine (DMAP), and 70 mL of methylene chloride were placed in a 250 mL flask equipped with a funnel. The solution in the flask was cooled down to −40° C. with stirring, and a solution of 5.13 g of ethyl phosphorodichloridate (EOP) (distilled before use) in 20 mL of methylene chloride was added dropwise through the funnel. After addition was complete, the mixture was stirred at room temperature for four hours to form the homopolymer BHET-EOP.

A solution of 1.60 g of terephthaloyl chloride (TC) (obtained from Aldrich Chemical Company and recrystallized with hexane before use) in 20 mL of methylene chloride was then added drop by drop. The temperature was brought up to about 45–50° C. gradually, and the reaction mixture was kept refluxing overnight to complete the copolymerization of the homopolymer poly(BHET-EOP) with the additional monomer TC to form the copolymer poly(BHET-EOP/TC).

The solvent was then evaporated, and the residue was redissolved in about 100–200 mL of chloroform. The chloroform solution was washed with a saturated NaCl solution three times, dried over anhydrous $Na_2SO_4$, and quenched into ether. The resulting precipitate was redissolved in chloroform and quenched again into ether. The resulting tough, off-white solid precipitate was filtered off and dried under vacuum. Yield 82%.

The structure of poly(BHET-EOP/TC, 80/20) was ascertained by $^1$H-NMR, $^{31}$P-NMR and FT-IR spectra. The structure was also confirmed by elemental analysis, which correlated closely with theoretical ratios. Exemplary structures may be found in published PCT application WO 98/44021.

The molecular weight of poly(BHET-EOP/TC, 80/20) was first measured by gel permeation chromatography (GPC) with polystyrene as the calibration standard. The resulting graph established a weight average molecular weight (Mw) of about 6100 and a number average molecular weight (Mn) of about 2200. Vapor pressure osmometry ("VPO") for this copolymer gave an Mn value of about 7900.

Example 2

Other Diol Variations

Diol terephthalates that are structurally related to that of BHET were synthesized by reacting TC with either n-propylenediol or 2-methylpropylenediol, the structures of which are shown below, to form the corresponding diol terephthalate.

—CH₂CH₂CH₂—

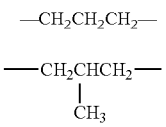

These diol terephthalates were then reacted with EOP to form the corresponding homopolymers. The homopolymers so formed were then used to produce the copolymers of the invention in a second reaction with TC.

Example 3

In vitro Release of Paclitaxel from Poly(BHET-EOP/TC) Copolymer

The polymer poly(bis-hydroxyethyl terephthalate-co-ethyl phosphate/terephthalate chloride (80:20) ["poly(BHET-EOP/TC, 80/20)"] was prepared as described above in Example 1. Both the polymer and paclitaxel were dissolved in $CH_2Cl_2$. The solution was cast into a cold Teflon® mold, then dried under a vacuum at room temperature for 48 hours. The film was then removed from the mold. FIG. 1 shows paclitaxel release from the film of poly(BHET-EOP/TC, 80/20) in phosphate buffer saline at 37° C.

Example 4

Preparation of Poly(BHDPT-EOP/TC, 50/50) Microspheres Containing Lidocaine

An aqueous solution of 0.5% w/v polyvinyl alcohol (PVA) was prepared in a 600 mL beaker by combining 1.35 g of PVA with 270 mL of deionized water. The solution was stirred for one hour and filtered. A copolymer/drug solution was prepared by combining 900 mg of poly(BHDPT-EOP/TC, 50/50) copolymer and 100 mg of lidocaine in 9 mL of methylene chloride and vortex-mixing.

While the PVA solution was being stirred at 800 rpm with an overhead mixer, the polymer/drug mixture was added dropwise. The combination was stirred for one and a half hours. The microspheres thus formed were then filtered, washed with deionized water, and lyophilized overnight. The experiment yielded 625 mg of microspheres loaded with 3.7% w/w lidocaine.

Lidocaine-containing microspheres were also prepared from poly(BHDPT-HOP/TC, 50/50) by the same process. This experiment yielded 676 mg of microspheres loaded with 5.3% w/w lidocaine.

Example 5

Synthesis of Poly(L-lactide-co-ethyl-phosphate) [Poly(LAEG-EOP)]

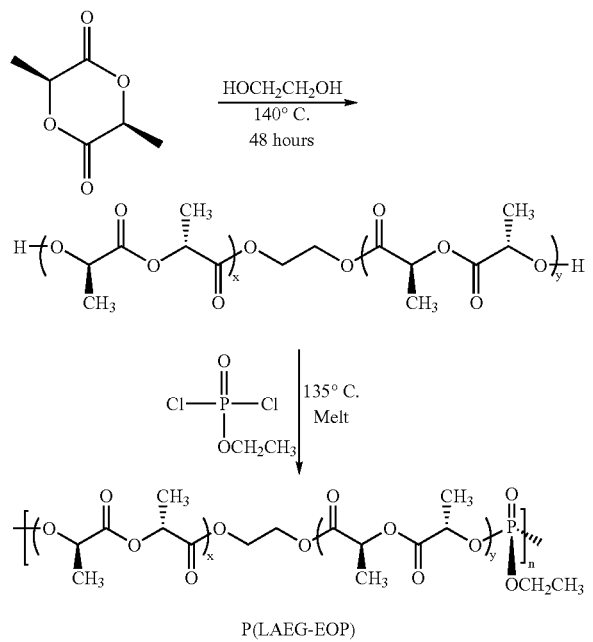

P(LAEG-EOP)

20 g (0.139 mole of (3S)-cis-3,6-dimethyl-1,4-dioxane-2,5-dione (L-lactide) (obtained from Aldrich Chemical Company, recrystallized with ethyl acetate, sublimed, and recrystallized with ethyl acetate again) and 0.432 g (6.94 mmole) of ethylene glycol (99.8%, anhydrous, from Aldrich) were placed in a 250 mL round-bottomed flask flushed with dried argon. The flask was closed under vacuum and placed in an oven heated to 140° C. The flask was kept at this temperature for about 48 hours with occasional shaking.

The flask was then filled with dried argon and placed in oil bath heated to 135° C. Under an argon stream, 1.13 g of ethyl phosphorodichloridate was added with stirring. After one hour of stirring, a low vacuum (about 20 mm Hg) was applied to the system, and it was allowed to stand overnight. One hour before work-up, a high vacuum was applied. After cooling, the polymer was dissolved in 200 mL of chloroform and quenched into one liter of ether twice to an off-white precipitate, which was dried under vacuum.

It was confirmed by NMR spectroscopy that the polymer obtained was the desired product, poly(L-lactide-co-ethyl-phosphate) [poly(LAEG-EOP)].

Example 6

Preparation of Poly(LAEG-EOP) Microspheres Containing Lidocaine Using Polyvinyl Alcohol as the Non-Solvent Phase A solution of 0.5% w/v polyvinyl alcohol (PVA) in deionized water solution was prepared in a 600 mL beaker by combining 1.05 g of PVA with 210 mL of deionized water. The solution was stirred for one hour and filtered. A polymer/drug solution was prepared by combining 630 mg of polymer and 70 mg of lidocaine in 7 mL of methylene chloride and mixing by vortex. The PVA solution was mixed at 500 rpm with an overhead mixer, and the polymer/drug solution was added dropwise. After 30 minutes of mixing, 200 mL of cold deionized water was added to the stirring PVA solution. The resulting mixture was stirred for a total of 3.5 hours. The microspheres formed were filtered off, washed with deionized water, and lyophilized overnight. Microspheres loaded with 4.2% w/w lidocaine were thus obtained.

Example 7

Synthesis of Poly(DAPG-EOP)

The d,l racemic mixture of poly(L-lactide-co-propyl-phosphate) ["poly(DAPG-EOP)"] was prepared as follows:

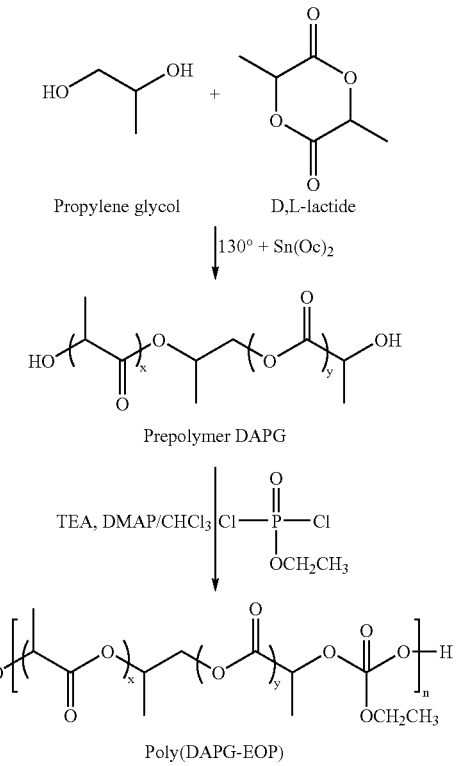

The product was obtained as a white solid soluble in organic solvents. Depending on reaction conditions, different intrinsic viscosities and different molecular weights were obtained, as shown below in summary form:

| Base(s) | Reaction Time/Temp | Eq EOPCl$_2$ | Mw | IV |
|---|---|---|---|---|
| 2.5 eq TEA; 0.5 eq DMAP | 15 mins/ room - temp. | 1.05 | — | 0.42 |
| 2.5 eq TEA; 0.5 eq DMAP | 18 hrs/ reflux | 1.05 | — | 0.27 |
| 2.5 eq TEA; 0.5 eq DMAP | about 2.5 days/ reflux | 1.05 | — | 0.39 |
| 2.5 eq TEA; 0.1 eq DMAP | 1 h/4° C.; 2 h/room temp. | 1.01 | — | 0.06 |
| 2.5 eq TEA; 0.5 eq DMAP | 1 h/4° C.; 2 h/room temp. | 1.01 | 91,100 | 0.47 |
| 2.5 eq TEA; 0.5 eq DMAP | 1 h/4° C.; 2 h/room temp. | 1.01 | 95,900 (Mn 44,200; Mw/Mn 2.2) | 0.42 |
| 1.1 eq DMAP | 1 h/4° C.; 2 h/room temp. | 1.01 | — | 0.08 |
| 1.5 eq TEA; 0.5 eq DMAP | 1 h/4° C.; 2 h/room temp. | 1.01 | — | 0.23 |
| 2.5 eq TEA; 0.5 eq DMAP | 1 h/4° C.; 17 h/room temp. | 1.00 | 28,400 | 0.25 |
| 2.5 eq TEA; 0.5 eq DMAP | 1 h/4° C.; 2 h/room temp. | 1.00 | 26,800 (Mn 12,900; Mw/Mn 2.1) | 0.23 |
| 2.5 eq TEA; 0.5 eq DMAP | 1 h/4° C.; 2 h/room temp. | 1.01 | 14,700 | 0.16 |
| 2.5 eq TEA; 0.5 eq DMAP | 1 h/4° C.; 2 h/room temp. | 1.01 | 32,200 (Mn 13,000; Mw/Mn 2.5) | 0.32 |
| 3.0 eq DMAP | 1 h/4° C.; 2 h/room temp. | 1.00 | — | 0.20 |
| 2.5 eq TEA; 0.5 eq DMAP | 1 h/4° C.; 2 h/room temp. | 1.00 | — | 0.22 |

Example 8

Preparation of Poly(DAEG-EOP) Microspheres With Lidocaine Using Silicon Oil as the Non-solvent Phase Two percent sorbitan-trioleate, which is commercially available from Aldrich under the tradename Span-85, in silicon oil was prepared in a 400 mL beaker by combining 3 mL of Span-85 with 150 mL of silicone oil and mixing with an overhead stirrer set at 500 rpm. A d,l racemic mixture of poly(L-lactide-co-ethyl-phosphate) poly(DAEG-EOP) polymer/drug solution was prepared by dissolving 400 mg of the polymer prepared by the method described above in Example 5, and 100 mg of lidocaine in 4.5 mL of methylene chloride. The resulting polymer/drug solution was added dropwise to the silicone oil/span mixture with stirring. The mixture was stirred for an hour and 15 minutes. The microspheres thus formed were filtered off and washed with petroleum ether to remove the silicone oil/span mixture, and lyophilized overnight.

450 mg of microspheres loaded with 7.6% w/w lidocaine were thus obtained. Approximately 10 mg of microspheres were placed in phosphate buffer saline (0.1M, pH 7.4) at 37° C. on a shaker and sampled regularly. The results were plotted as % lidocaine released vs. time in days.

Figure 2A:
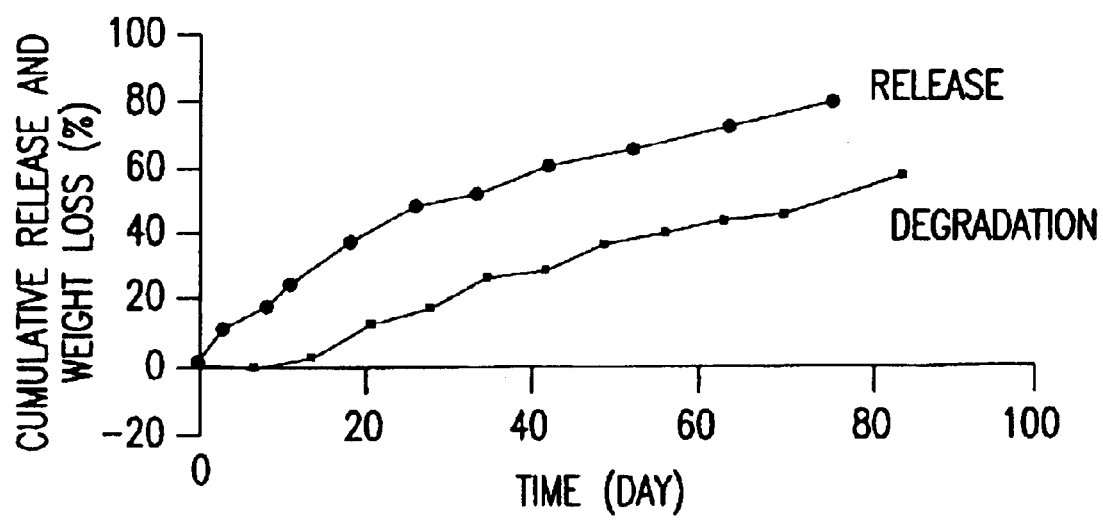
FIG. 2A through 2C all show degradation data of poly (D,L-lactide-co-ethyl phosphate) ["poly(DAPG-EOP)"] polymers.
Figure 2B:
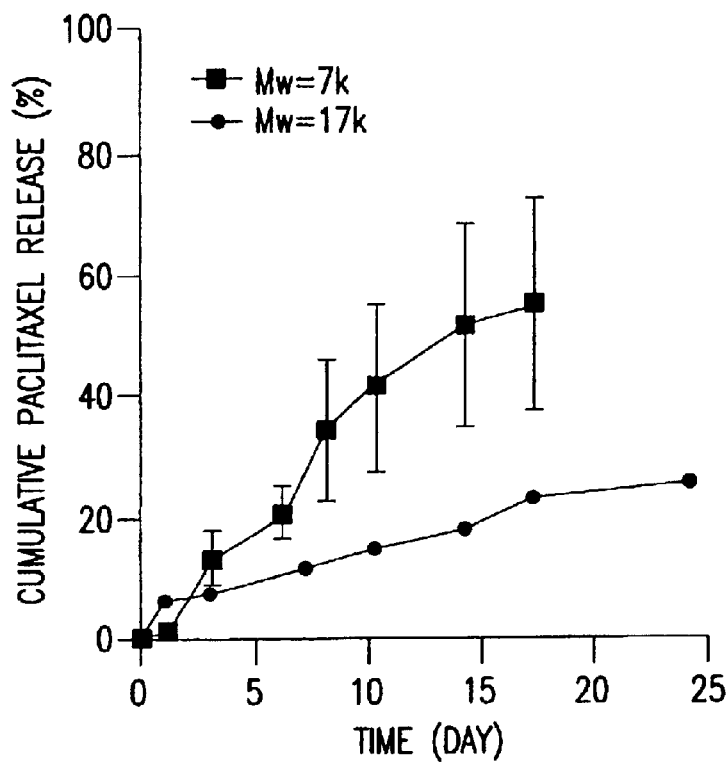
Figure 2C:
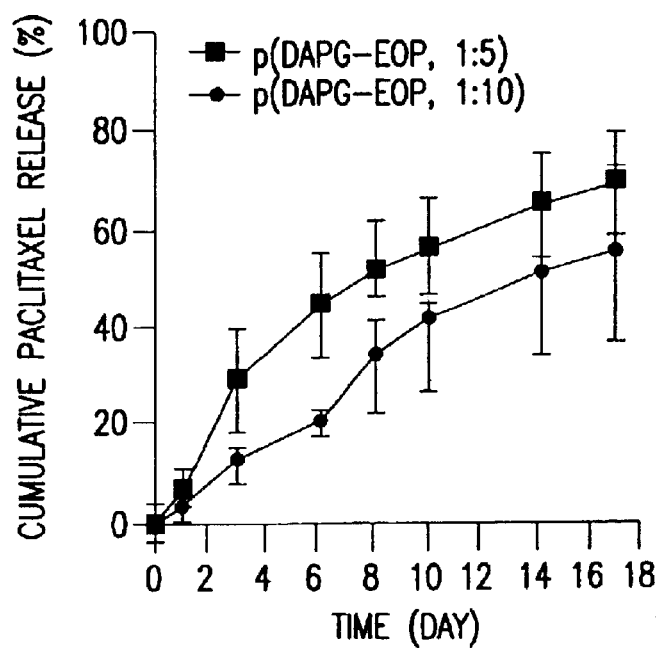

Similar data for poly(DAPG-EOP) microspheres containing paclitaxel was obtained, as shown in FIGS. 2A, 2B and 2C.

Example 9

Biocompatibility of Poly(DAPG-EOP) Microspheres in Mouse Peritoneal Cavity

The biocompatibility of biodegradable poly(phosphoester) microspheres of the invention was tested as follows:

Three 30 mg/mL samples of lyophilized poly(L-lactide-co-ethyl-phosphate) microspheres were prepared by the method described above in Example 10, the first having diameters greater than 75 microns, the second having diameters within the range of 75–125 microns, and the third having diameters within the range of 125–250 microns. Each sample was injected intra-peritoneally into a group of 18 female CD-1 mice having a starting body weight of 25 g. Animals in each group were weighed, sacrificed, and necropsied at 2, 7 and 14 days, and at 1, 2 and 3 months. Any lesions detected during the necropsy were graded on a scale of 0 to 4, with 0 indicating no response to treatment and 4 indicating a severe response to treatment.

Inflammatory lesions were observed to be restricted to an association with the microspheres on peritoneal surfaces or within fat tissue, and were compatible with foreign body isolation and encapsulation. Focal to multifocal supportive peritoneal steatitis with mesothelial hyperplasia was observed at 2–7 days, but gradually resolved by macrophage infiltration, the formation of inflammatory giant cells, and fibrous encapsulation of the microspheres at later sacrifices. Occasional adherence of microspheres to the liver and diaphragm, with associated inflammatory reaction, was also seen. Lesions related to microspheres were not seen within abdominal or thoracic organs. Microspheres, which were detected throughout the duration of the study, appeared transparent at early sacrifices but, at later times, developed crystalline material internally. No effects on body growth were observed. The peritoneal reaction was observed to be limited to areas directly adjacent to the microspheres with no apparent deleterious effects on major thoracic or abdominal organs.

Similar intraperitoneal injection of DAPG-EOP into male and female S-D rats gave the following results:

| Dose Level | Test | Initial No. in Test | | Cumulative Mortality[a] | |
|---|---|---|---|---|---|
| (mg/kg) | Material | M | F | M | F |
| 0 | 10% Dextran 40 in 0.9% Saline | 25 | 25 | 0 | 0 |
| 30 | DAPG-EOP | 25 | 25 | 1 | 0 |
| 100 | DAPG-EOP | 25 | 25 | 0 | 0 |
| 300 | DAPG-EOP | 25 | 25 | 0 | 0 |

[a]Represents animals found dead or sacrificed in moribund condition during study period.
M = Male;
F = Female

Example 10

Synthesis of the Poly(Phosphoester) Poly(trans-CHDM-HOP)

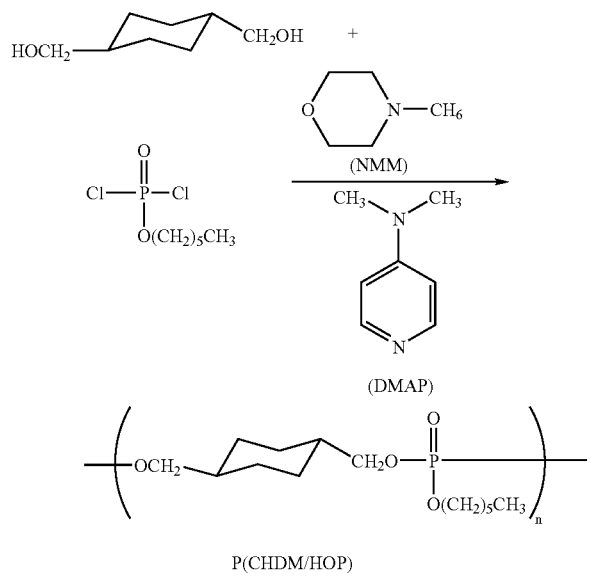

P(CHDM/HOP)

Under an argon stream, 10 g of trans-1,4-cyclohexane dimethanol (CHDM), 1.794 g of 4-dimethylaminopyridine (DMAP), 15.25 ml (14.03 g) of N-methyl morpholine (NMM), and 50 ml of methylene chloride, were transferred into a 250 ml flask equipped with a funnel. The solution in the flask was cooled down to −15° C. with stirring, and a solution of 15.19 g of hexyl phosphorodichloridate (HOP) in 30 ml of methylene chloride was added through the funnel. The temperature of the reaction mixture was raised to the boiling point gradually and maintained at reflux temperature overnight.

The reaction mixture was filtered, and the filtrate was evaporated to dryness. The residue was re-dissolved in 100 ml of chloroform. This solution was washed with 0.1 M solution of a mixture of HCl and NaCl, dried over anhydrous $Na_2SO_4$, and quenched into 500 ml of ether. The resulting flowable precipitate was collected and dried under vacuum to form a clear pale yellow gelatinous polymer with the flow characteristics of a viscous syrup. The yield for this polymer was 70–80%. The structure of poly(trans-CHDM-HOP) was ascertained by $^{31}$P-NMR and $^1$H-NMR spectra and by FT-IR spectra. The molecular weights (Mw=8584; Mn=3076) were determined by gel permeation chromatography (GPC) using polystyrene as a calibration standard.

Example 11

Incorporating Paclitaxel into Poly(CHDM-HOP) or Poly(CHDM-EOP)

100 mg of each of the polymers poly(CHDM-HOP) and poly(CHDM-EOP) was dissolved in ethanol at a concentration of about 50%. After the polymer was completely dissolved, 5 mg of paclitaxel powder (a chemotherapeutic drug) was added to the solution and stirred until the powder was completely dissolved. This solution was then poured into ice water to precipitate the polymer composition. The resulting suspension was centrifuged, decanted, and lyophilized overnight, to obtain a viscous gelatinous product.

Example 12

In Vitro Release of Paclitaxel from Poly(CHDM-HOP) and Poly(CHDM-EOP)

The following two polymers were prepared:
Poly(CHDM-EOP) and
Poly (CHDM-HOP)

Paclitaxel was blended with each polymer at a 10% loading level at room temperature to form a homogeneous paste. In a 1.7 mL plastic micro centrifuge tube, 5 mg of both of the paclitaxel polymer formulations to be tested was incubated with 1 mL of a buffer mixture of 80% PBS and 20% PEG 400 at 37° C. Four samples of each formulation to be tested were prepared. At specific time points, approximately every day, the PBS:PEG buffer was poured off for paclitaxel analysis by HPLC, and fresh buffer was added to the microcentrifuge tube. The release study was terminated at day 26, at which point the remaining paclitaxel in the polymer was extracted with a solvent to do a mass balance on paclitaxel.

When release studies for the release of paclitaxel from both polymers were performed, the total paclitaxel recovery was 65% for the poly(CHDM-HOP) formulation and 75% for the poly(CHDM-EOP) formulation.

Example 13

Preparation of p(DAPG-EOP) Microspheres Containing Paclitaxel by Solvent Dilution Method A solvent dilution (evaporation) method was used in the preparation of p(DAPG-EOP) microspheres containing paclitaxel. Approximately 10 grams of paclitaxel and 90 grams of polymer were weighed and dissolved in 250 ml of ethyl acetate. To prepare the non-solvent phase, ethyl acetate (90 ml) was added to 1 liter of 0.5% PVA and homogenized for 1 minute. The drug-polymer solution and the PVA-ethyl acetate solution were transferred through an in-line homogenizer into a flask. The solutions were stirred with an overhead stirrer. Approximately 900 ml of water was then added to the flask. The solution was then stirred for 30 minutes. The microsphere suspension was transferred to a filtering/drying unit containing 150 μm and 25 μm sieves. The microspheres were rinsed with one liter of de-ionized water and dried overnight. The dried microspheres on the 25 μm sieve were collected into a container.

Example 14

Preparation of p(DAPG-EOP) Microspheres Containing Paclitaxel by Solvent Evaporation Method Paclitaxel (10.08 g) and polymer (90.1 g) were weighed and dissolved in enough ethyl acetate to achieve a total volume of 250 ml. Ethyl acetate (90 ml) was added to one liter of 0.5% PVA and homogenized for 1 minute. The drug-polymer solution and the PVA-ethyl acetate solution were transferred through an in-line homogenizer to a 12-liter, 3-necked flask. The solutions were stirred with an overhead stirrer. Vacuum and air were used to evaporate the ethyl acetate. The vacuum and air were turned off after 40 minutes due to excessive foaming. Stirring was continued for an additional 20 minutes. The microsphere suspension was transferred to a filtering/drying unit containing 250 μm and 25 μm sieves and rinsed with one liter of de-ionized water. The material left on the 25 μm sieve was washed with de-ionized water into two one-liter centrifuge bottles and allowed to settle. After settling, the supernatant was discarded and the microspheres were frozen at −40° C. for 1 hour and then lyophilized for 72 hours.

Example 15

Preparation of p(DAPG-EOP) Microspheres Containing Paclitaxel by Spray Drying Method P(DAPG-EOP) is dissolved in methylene chloride at 5–20% (w/v) concentration. Paclitaxel is added to the polymer solution to achieve a final paclitaxel loading of 10% (w/w). After the drug is completely dissolved, the solution is spray dried using a Büchi spray drier. The resulting microspheres are collected.

Example 16

Preparation of p(DAPG-EOP) Microspheres Containing Lidocaine by Spray Drying Process P(DAPG-EOP) was dissolved in methylene chloride at 5–20% (w/v) concentration. Lidocaine was added to the polymer solution to achieve a final lidocaine loading of 10% (w/w). After the drug was completely dissolved, the solution was spray dried using a Büchi spray drier. Product was collected.

Example 17

In Vitro Release of Paclitaxel from Poly(DAPG-EOP)

The in vitro release of paclitaxel from the microspheres was carried out in phosphate buffered saline (pH 7.4) at 37° C. To maintain a sink condition, an octanol layer was placed on top of the PBS to continuously extract the released paclitaxel from the aqueous phase. The released paclitaxel was quantified using an HPLC method, and the in vitro mass loss of the polymer was obtained by a gravimetric method.

The results are shown in FIG. 2A.

Example 18

Comparative Studies of Sustained Release of Paclitaxel on A549 Tumors in an In Vivo Model A murine tumor nodule model, a widely used and accepted model for investigating the efficacy of therapies for solid tumors, was used to establish the utility of sustained release for solid tumors. Athymic nude Balb/c mice were engrafted with human non-small cell lung cancer cell lines (A549 and H1299, both of which were obtained from the American Type Culture Collection).

The cells were grown to confluence in DMEM/F12 medium (Mediatech, Herndon, Va.) supplemented with 10% fetal bovine serum ("growth medium") under antibiotic-free conditions at 37° in a 5% $CO_2$ atmosphere. After growing under standard these tissue culture conditions, the cells were enzymatically detached, enumerated, and the concentration was adjusted as required.

The cells were mixed 1:1 with Matrigel™ as an enhancer for engraftment, and $2 \times 10^6$ cells were injected subcutaneously on the flanks. Tumors were allowed to grow until achieving a volume of approximately 200–400 mm$^3$, as determined by the formula:

Tumor volume=(length)×(width)×(height)

The dimensions of the tumor on each test animal were measured directly with calipers.

Various formulations of paclitaxel were administered to the test animals bearing tumors, either systemically or intratumorally. Each animal was weighed at the time of treatment so that dosages could be adjusted to achieve the mg/kg amounts reported. Systemic administration was achieved by injecting the test composition into the intraperitoneal cavity of the test animal. For intraperitoneal ("IP") injections, the animals received a total injection volume of approximately 1 mL.

Intratumoral administration ("IT"), on the other hand, was accomplished by the following procedure:

(1) injecting a single volume of about 100 µl (0.1 mL) the test composition into the center of the tumor nodule with a 21–25 gauge needle over a time period of about 10–20 seconds;

(2) infusing the volume over about 10–15 seconds, and then leaving the needle in place for an additional time of about 10–20 seconds; and (3) withdrawing the needle.

Following the treatments, all mice were tagged, and the tumors were measured three times weekly with calipers. Test animals were also weighed once weekly.

The various formulations tested were as follows:

(1) paclitaxel ("PTX") dissolved in 1:1 in 12.5% cremophor/12.5% ethanol and then diluted to the proper concentration with 0.9% NaCl (so that the injection volume was comparable for all groups), making a 115 mM solution of NaCl, ("conventional" formulation of paclitaxel); and (2) poly(DAPG-EOP) microspheres containing 0.1 mg paclitaxel/1 mg poly (DAPG-EOP) suspended in 10% dextran 40 diluent ("PTX/Poly").

Figure 3:
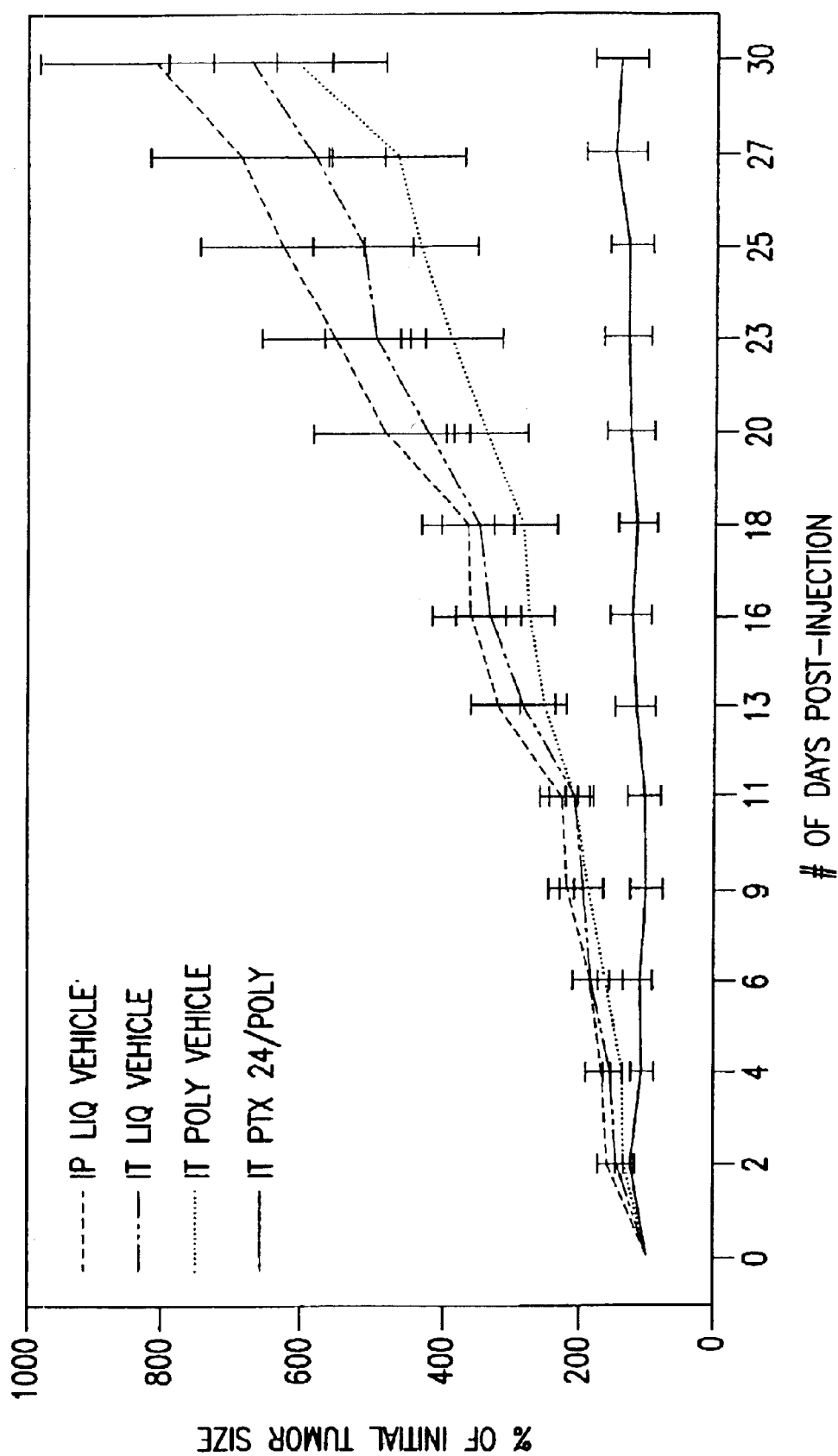
FIG. 3 shows the time-dependent change in A549 tumor nodules treated with 24 mg/kg paclitaxel in poly(DAPG-EOP) intratumorally and treated with the poly(DAPG-EOP) carrier alone.
Figure 4:
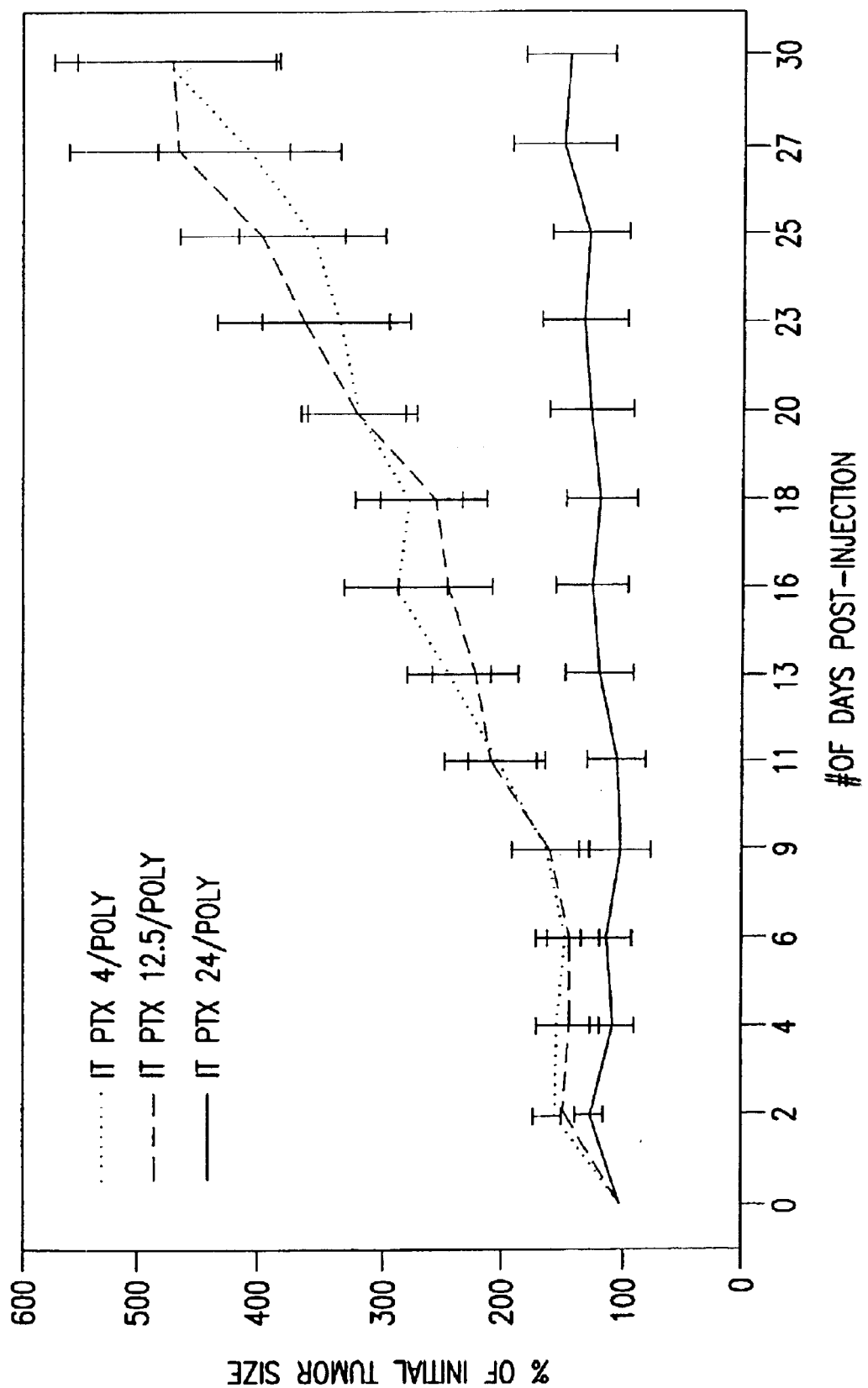
FIG. 4 shows the time-dependent change in A549 tumor nodules treated intratumorally with three different dosages of paclitaxel in poly(DAPG-EOP) (4 mg/kg, 12.5 mg/kg or 24 mg/kg).
Figure 5:
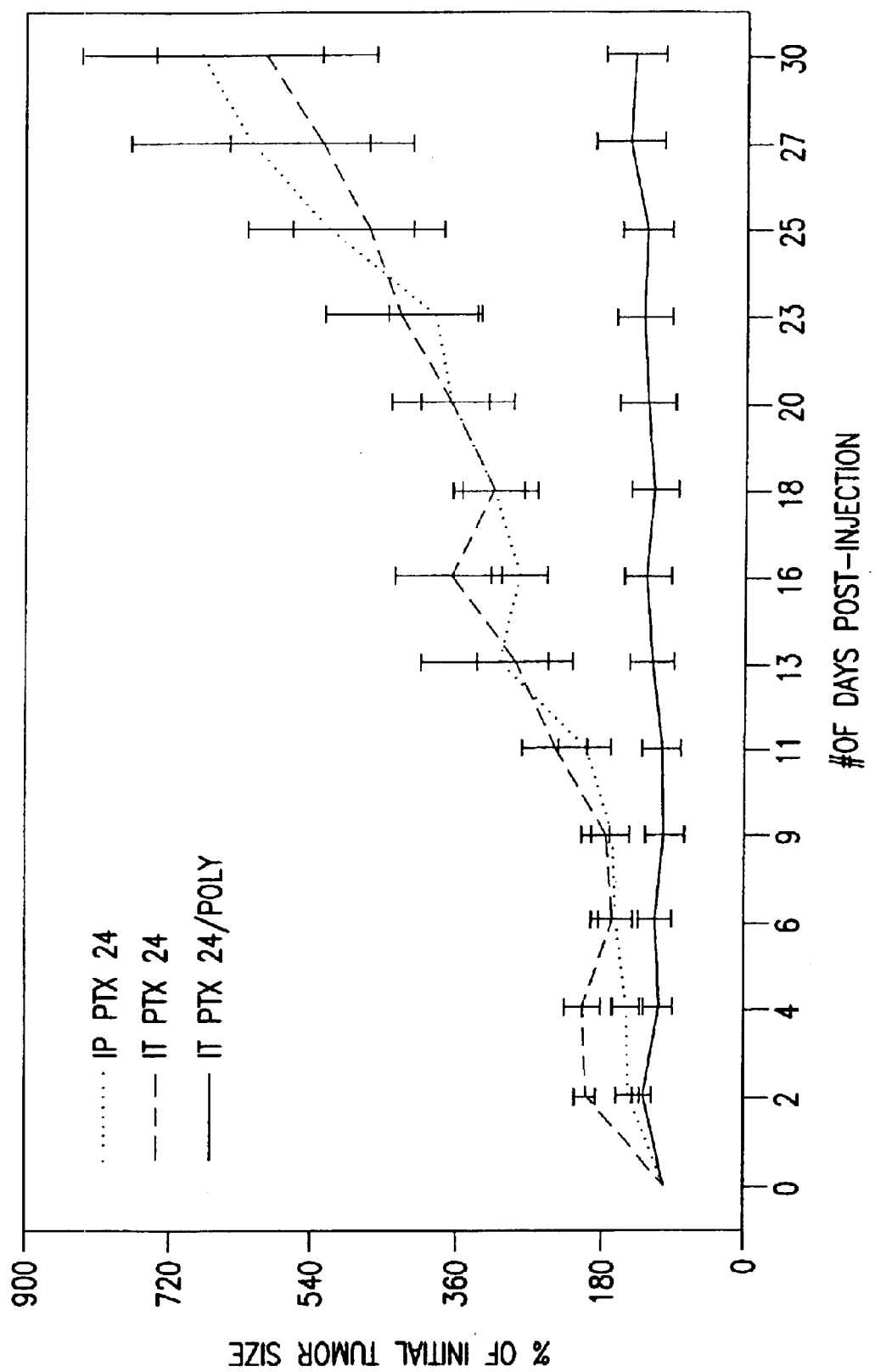
FIG. 5 shows the time-dependent change in A549 tumor nodules treated paclitaxel in its conventional liquid formulation (24 mg/kg) via intraperitoneal administration, paclitaxel in its conventional liquid formulation (24 mg/kg) administered intratumorally, and paclitaxel in poly(DAPG-EOP) (24 mg/kg) administered intratumorally.

The results are graphically depicted in FIGS. 3–5 as the mean of two experiments ±S.E.M. FIG. 3 compares the results of the following treatments:

IP Liq Vehicle=Intraperitoneal administration of conventional cremophor/ethanol vehicle with no paclitaxel (control);

IT Liq Vehicle=Intratumoral administration of cremophor/ethanol vehicle with no paclitaxel (control);

IT Poly Vehicle=Intratumoral administration of poly (DAPG-EOP) microspheres with no paclitaxel (control); and IT PTX 24/Poly=Intratumoral administration of 24 mg/kg paclitaxel in poly(DAPG-EOP) microspheres.

FIG. 4 compares the results of the following treatments:

IT PTX 4/Poly=4 mg/kg paclitaxel in poly(DAPG-EOP) microspheres injected intratumorally;

IT PTX 12.5/Poly=12.5 mg/kg paclitaxel in poly(DAPG-EOP) microspheres injected into tumor; and IT PTX 24/Poly=24 mg/kg paclitaxel in poly(DAPG-EOP) microspheres injected into tumor.

FIG. 5 compares the results of the following treatments:

IP PTX 24=Intraperitoneal injection of 24 mg/kg paclitaxel in conventional liquid formulation;

IT PTX 24=Intratumoral injection of 24 mg/kg paclitaxel in conventional liquid formulation; and IT PTX 24/Poly=Intratumoral injection of 24 mg/kg paclitaxel in poly(DAPG-EOP) microspheres.

Example 19

Comparative Studies of Sustained Release of Paclitaxel on H1299 Tumors in an In Vivo Model Time-dependent changes in H1299 tumor nodule growth and/or sizes following different treatments were determined.

Figure 6:
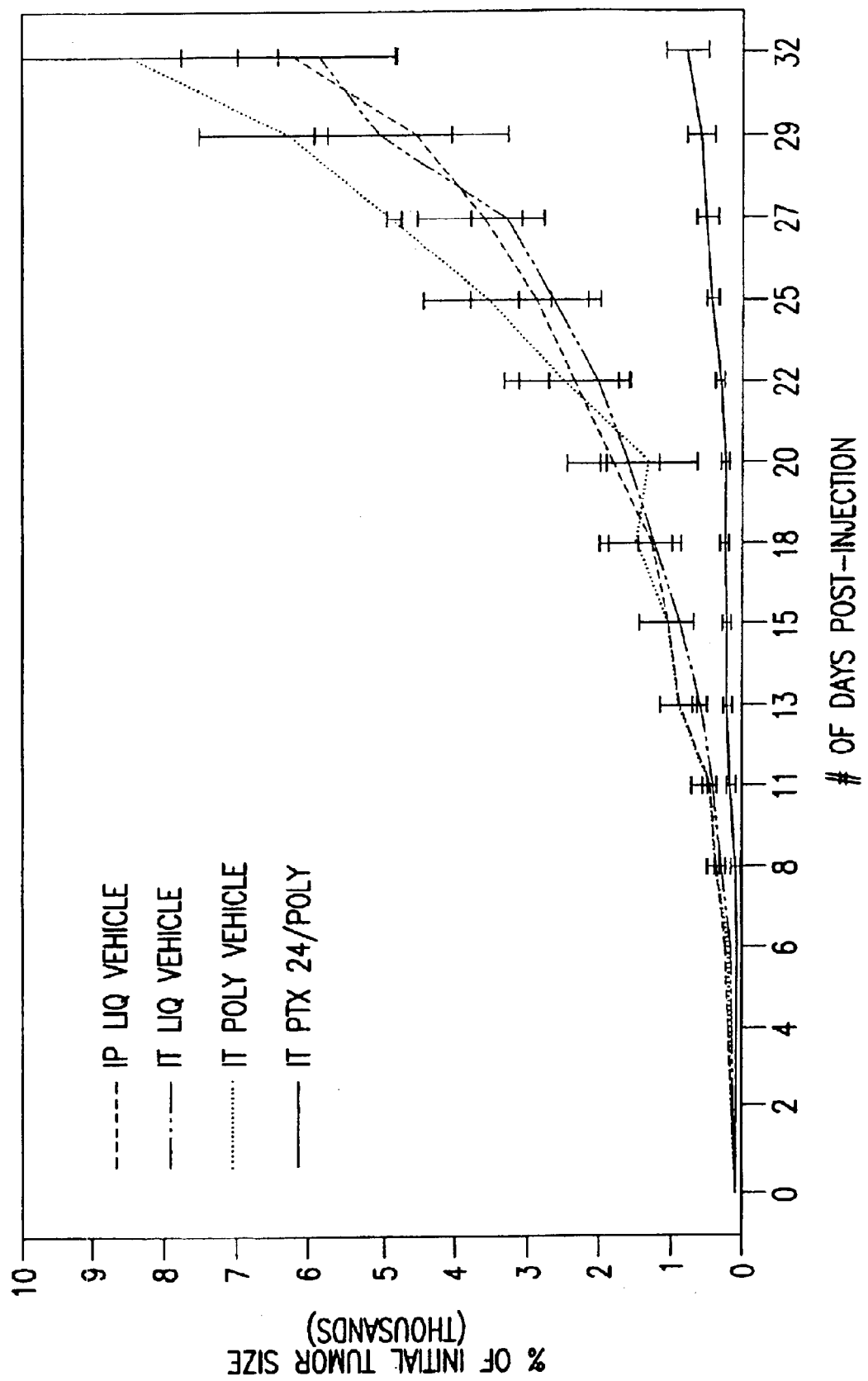
FIG. 6 shows the time-dependent change in H1299 tumor nodules treated with 24 mg/kg paclitaxel in poly(DAPG-EOP) intratumorally, and the poly(DAPG-EOP) polymer carrier alone.
Figure 7:
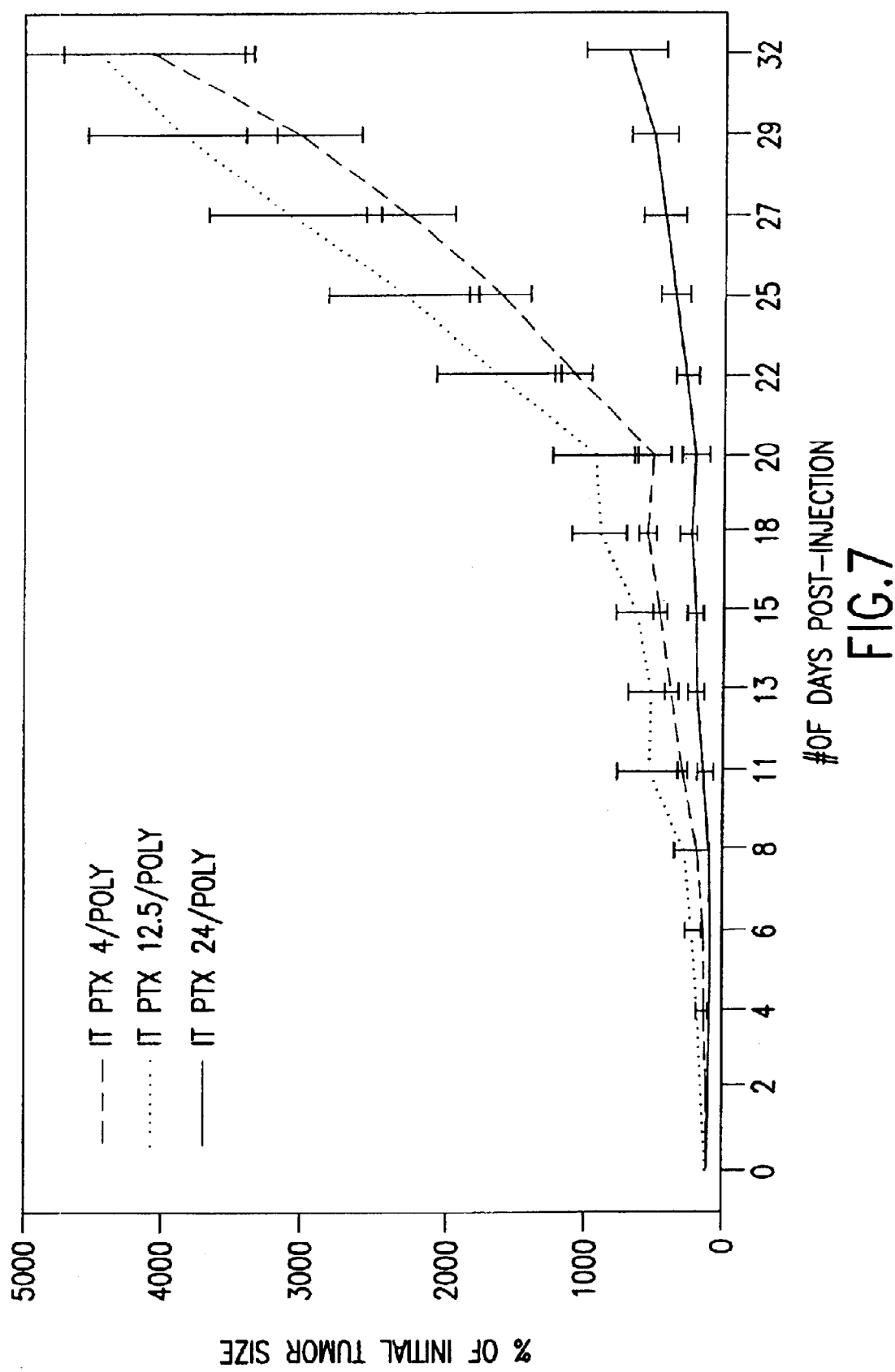
FIG. 7 shows the time-dependent change in H1299 tumor nodules treated intratumorally with three different dosages of paclitaxel in poly(DAPG-EOP) (4 mg/kg, 12.5 mg/kg or 24 mg/kg).
Figure 8:
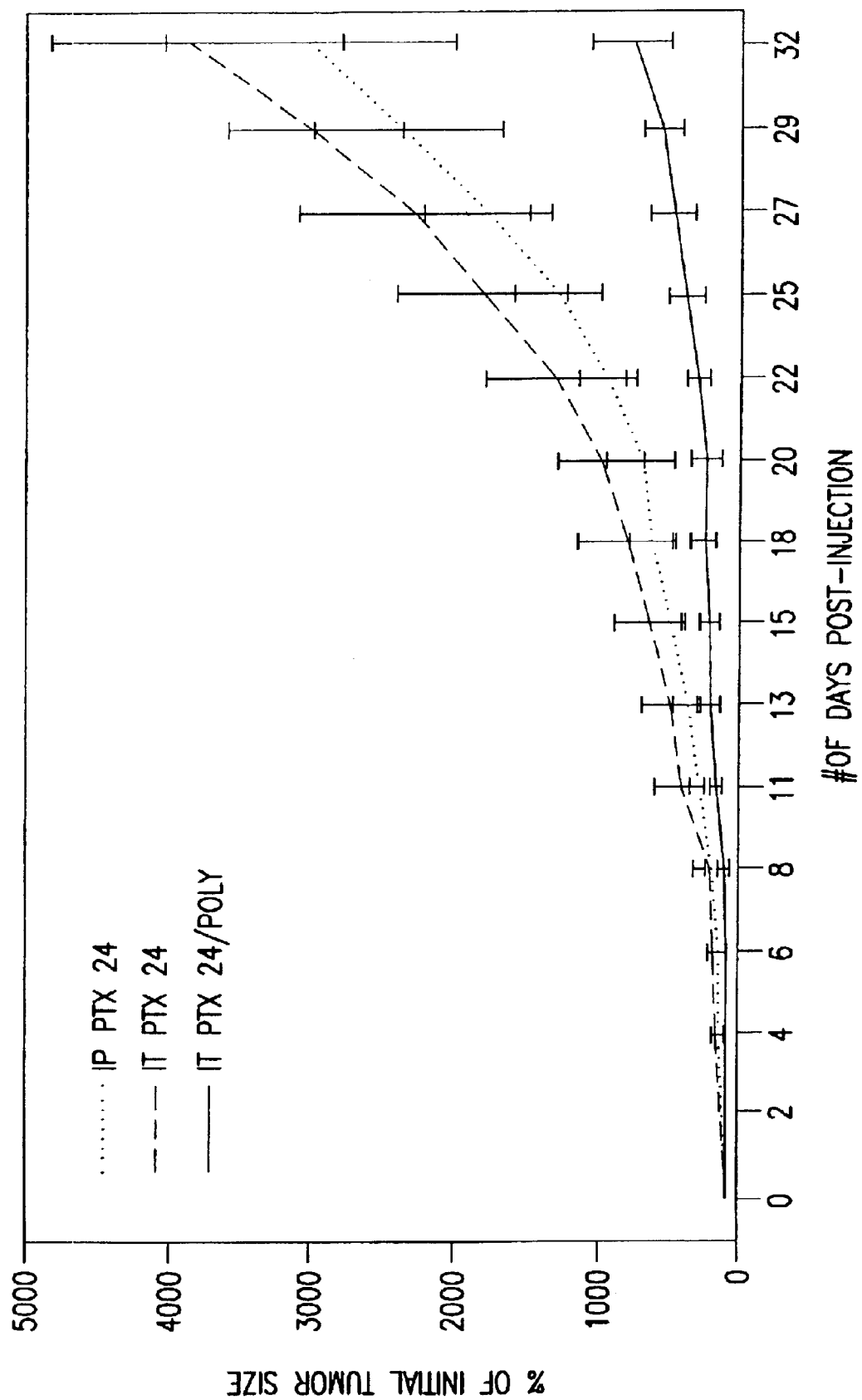
FIG. 8 shows the time-dependent change in H1299 tumor nodules treated paclitaxel in its conventional liquid formulation (24 mg/kg) via intraperitoneal administration, paclitaxel in its conventional liquid formulation (24 mg/kg) administered intratumorally, and paclitaxel in poly(DAPG-EOP) (24 mg/kg) administered intratumorally.

The results are graphically depicted in FIGS. 6–8 as the mean of two experiments ±S.E.M.

FIG. 6 compares the results of the following treatments:

IP Liq Vehicle=Intraperitoneal administration of conventional cremophor/ethanol vehicle with no paclitaxel (control);

IT Liq Vehicle=Intratumoral administration of cremophor/ethanol vehicle with no paclitaxel (control);

IT Poly Vehicle=Intratumoral administration of poly (DAPG-EOP) microspheres with no paclitaxel (control); and IT PTX 24/Poly=Intratumoral administration of 24 mg/kg paclitaxel in poly(DAPG-EOP) microspheres.

FIG. 7 compares the results of the following treatments, all administered intratumorally:

IT PTX 4/Poly=4 mg/kg paclitaxel in poly(DAPG-EOP) microspheres;

IT PTX 12.5/Poly=12.5 mg/kg paclitaxel in poly(DAPG-EOP) microspheres; and

IT PTX 24/Poly=24 mg/kg paclitaxel in poly(DAPG-EOP) microspheres.

FIG. 8 compares the results of the following treatments:

IP PTX 24=Intraperitoneal injection of 24 mg/kg paclitaxel in conventional liquid vehicle;

IT PTX 24=Intratumoral injection of 24 mg/kg paclitaxel in conventional liquid vehicle; and IT PTX 24/Poly=Intratumoral injection of 24 mg/kg paclitaxel in poly(DAPG-EOP) microspheres.

Example 20

Weight Changes in Mice Following Treatment

Animals treated with the procedures described above in Examples 18 and 19 were weighed at Day 0, Day 7, Day 14, Day 21 and Day 28 after the following treatments:

IP Liq Vehicle=Intraperitoneal administration of conventional cremophor/ethanol vehicle with no paclitaxel (control);

IP PTX 24=Intraperitoneal injection of 24 mg/kg paclitaxel in conventional cremophor/ethanol vehicle;

IT Liq Vehicle=Intratumoral administration of cremophor/ethanol vehicle with no paclitaxel (control);

IT PTX 24=Intratumoral injection of 24 mg/kg paclitaxel in conventional liquid vehicle;

IT Poly Vehicle=Intratumoral administration of poly (DAPG-EOP) microspheres with no paclitaxel (control); and IT PTX 24/Poly=Intratumoral injection of 24 mg/kg paclitaxel in poly(DAPG-EOP) microspheres.

Figure 9:
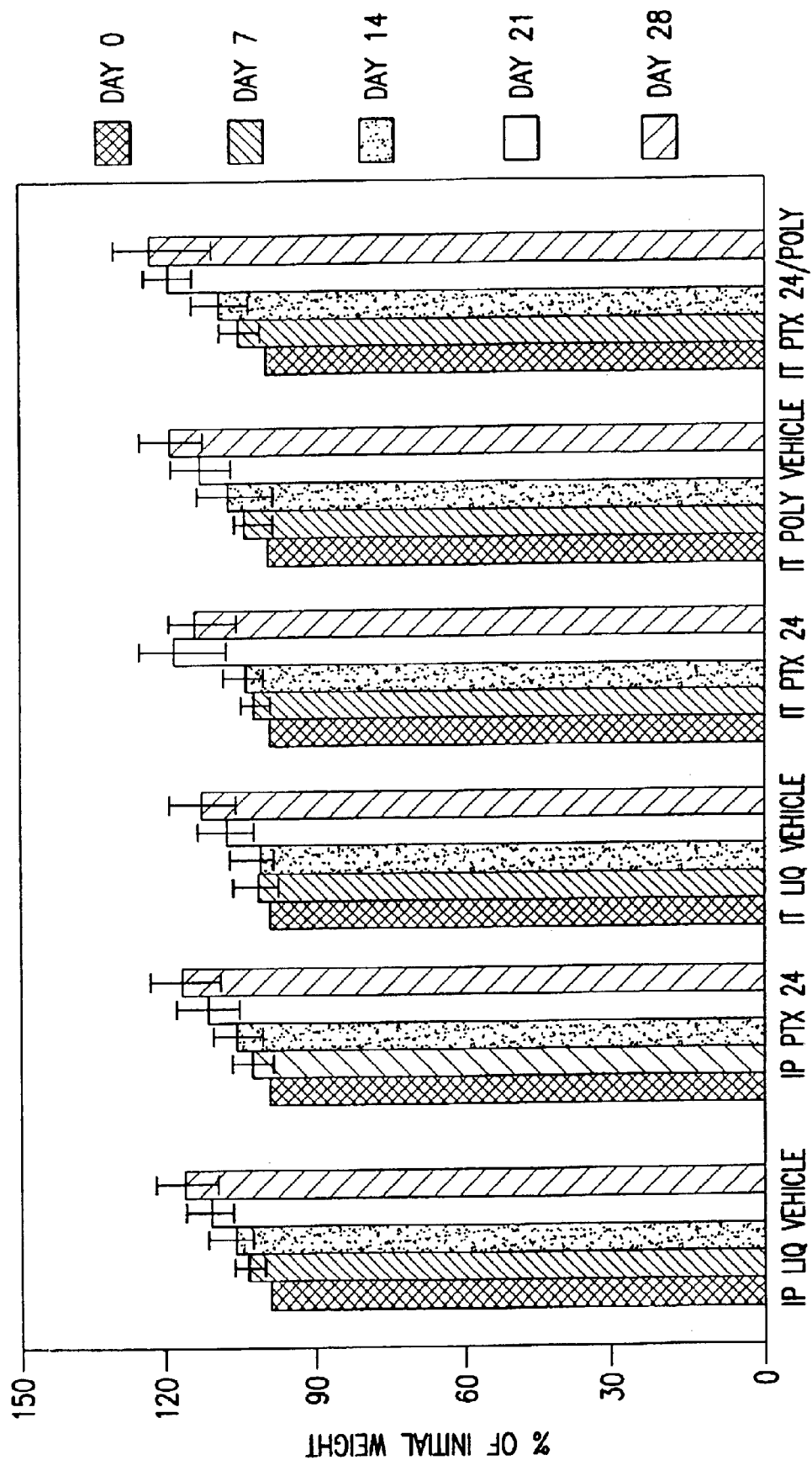
FIG. 9 shows the weight changes in A549 tumor-bearing mice following treatment with either a vehicle control or 24 mg/kg of paclitaxel in its conventional liquid formulation or in poly(DAPG-EOP).
Figure 10:
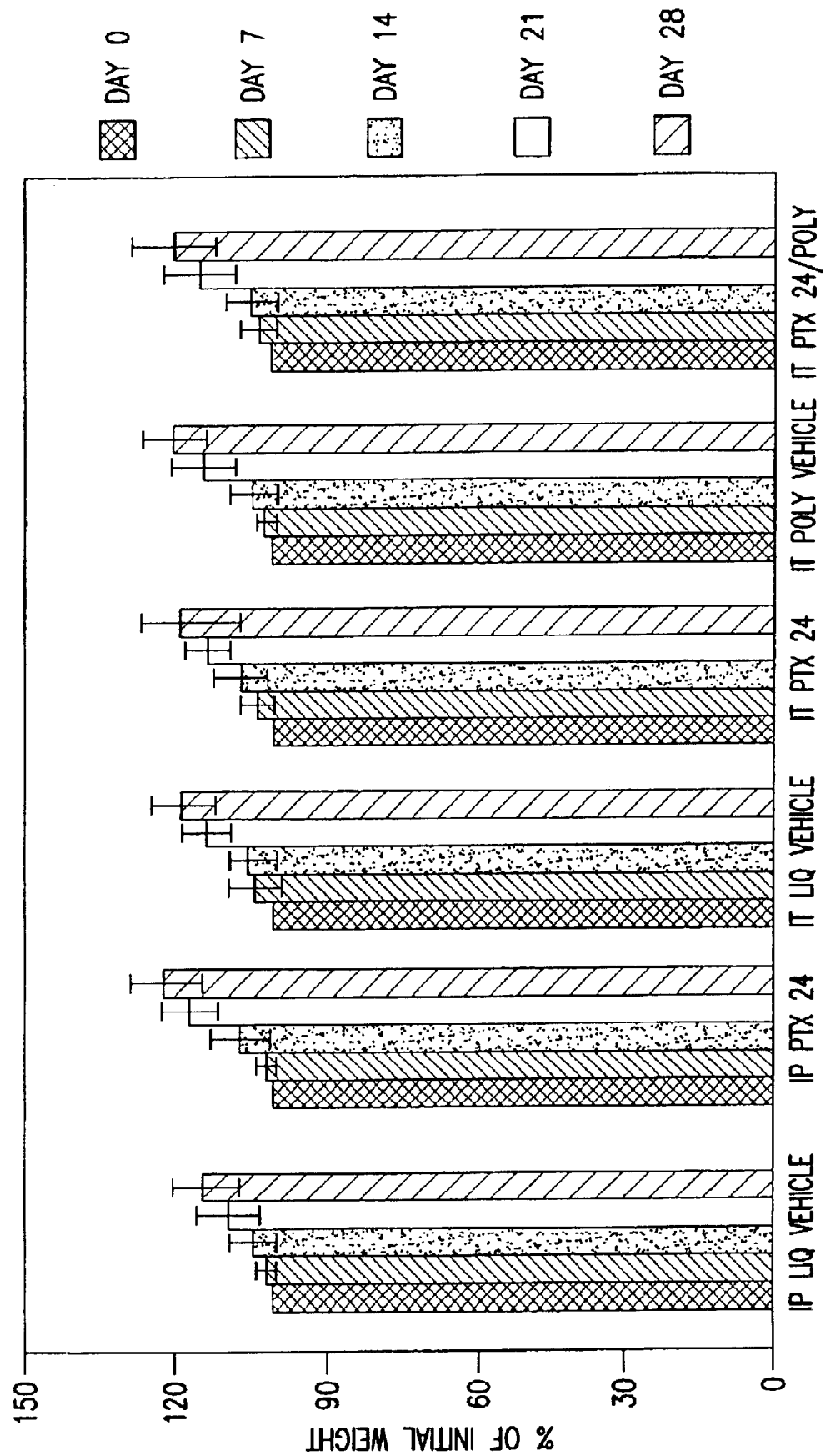
FIG. 10 shows the weight changes in H1299 tumor-bearing mice following treatment with either a vehicle control or 24 mg/kg paclitaxel in its conventional liquid formulation or poly(DAPG-EOP).

The results of a single experiment are presented graphically in FIG. 9 for the A549 cell line. The mean of two experiments ±S.E.M. for the H1299 cell line is shown in FIG. 10. Animal weights increased in all of the groups over time without significant differences between groups, and none of the treatment groups were associated with any overt toxicity.

Example 21

Tumor Doubling Time

Estimated tumor volume doubling times were derived from the data shown in FIGS. 3–8 described above. The P values shown represent the differences between the group referenced and the group receiving an intratumoral injection of 24 mg/kg paclitaxel in poly(DAPG-EOP) microspheres. The treatments referenced are the following:

IP Liq Vehicle=Intraperitoneal administration of conventional cremophor/ethanol vehicle without paclitaxel (control);

IP PTX 24=Intraperitoneal injection of 24 mg/kg paclitaxel in conventional cremophor/ethanol vehicle;

IT Liq Vehicle=Intratumoral injection of conventional cremophor/ethanol vehicle without paclitaxel (control);

IT PTX 4=Intratumoral injection of 4 mg/kg paclitaxel in cremophor/ethanol vehicle;

IT PTX 12=Intratumoral injection of 12 mg/kg paclitaxel in cremophor/ethanol vehicle;

IT PTX 24=Intratumoral injection of 24 mg/kg paclitaxel in cremophor/ethanol vehicle;

IT Poly Vehicle=Intratumoral administration of poly (DAPG-EOP) microspheres with no paclitaxel (control);

IT PTX 4/Poly=Intratumoral injection of 4 mg/kg paclitaxel in poly(DAPG-EOP) microspheres;

IT PTX 12/Poly=Intratumoral injection of 12 mg/kg paclitaxel in poly(DAPG-EOP) microspheres;

IT PTX 24/Poly=Intraperitoneal injection of 24 mg/kg paclitaxel in poly(DAPG-EOP) microspheres.

Figure 11:
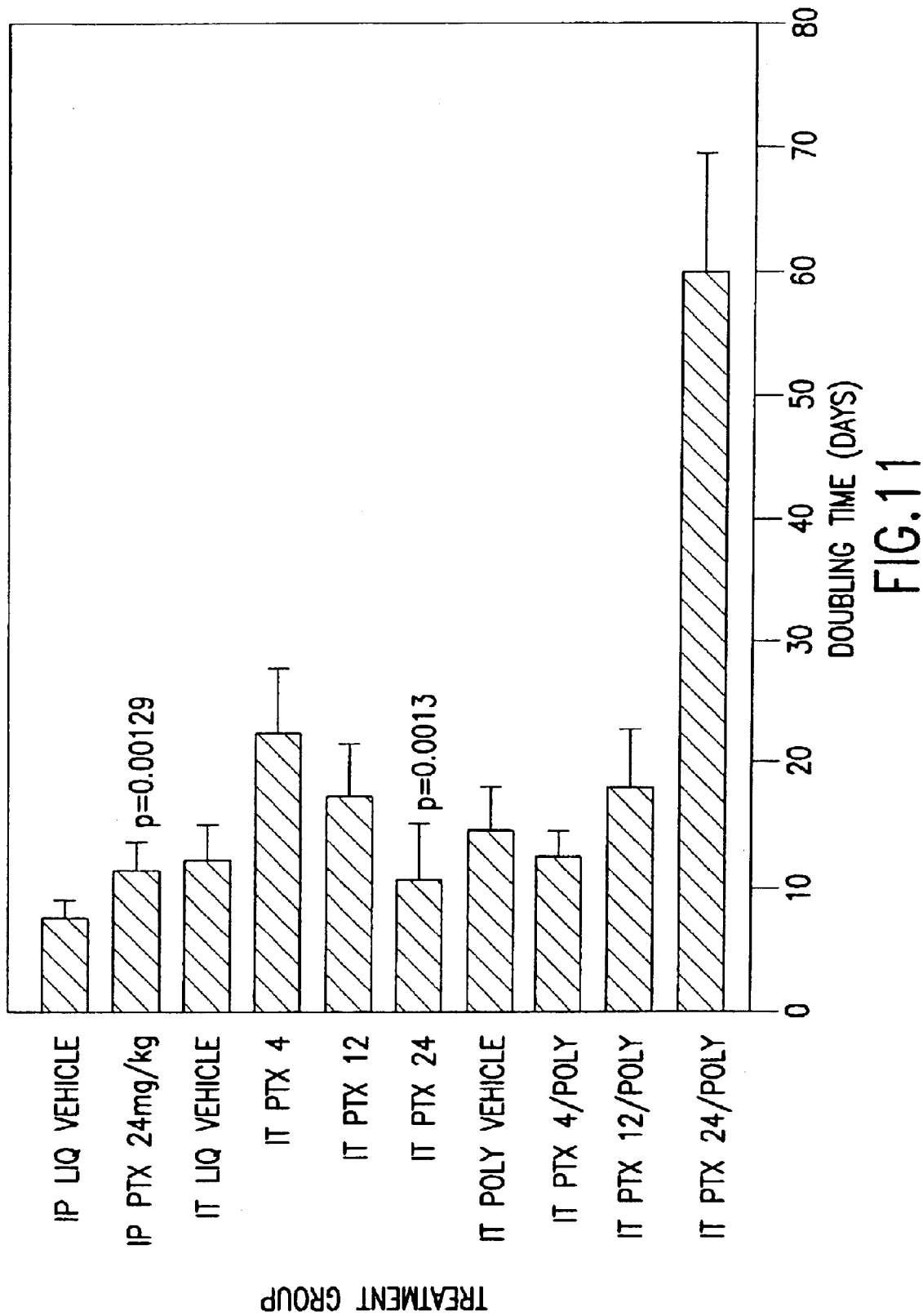
FIG. 11 shows estimated tumor volume doubling times based on data derived from that shown in FIGS. 4–6 for A549 tumor cells. P values shown represent the differences between the corresponding group and the 24 mg/kg group for paclitaxel in poly(DAPG-EOP).
Figure 12:
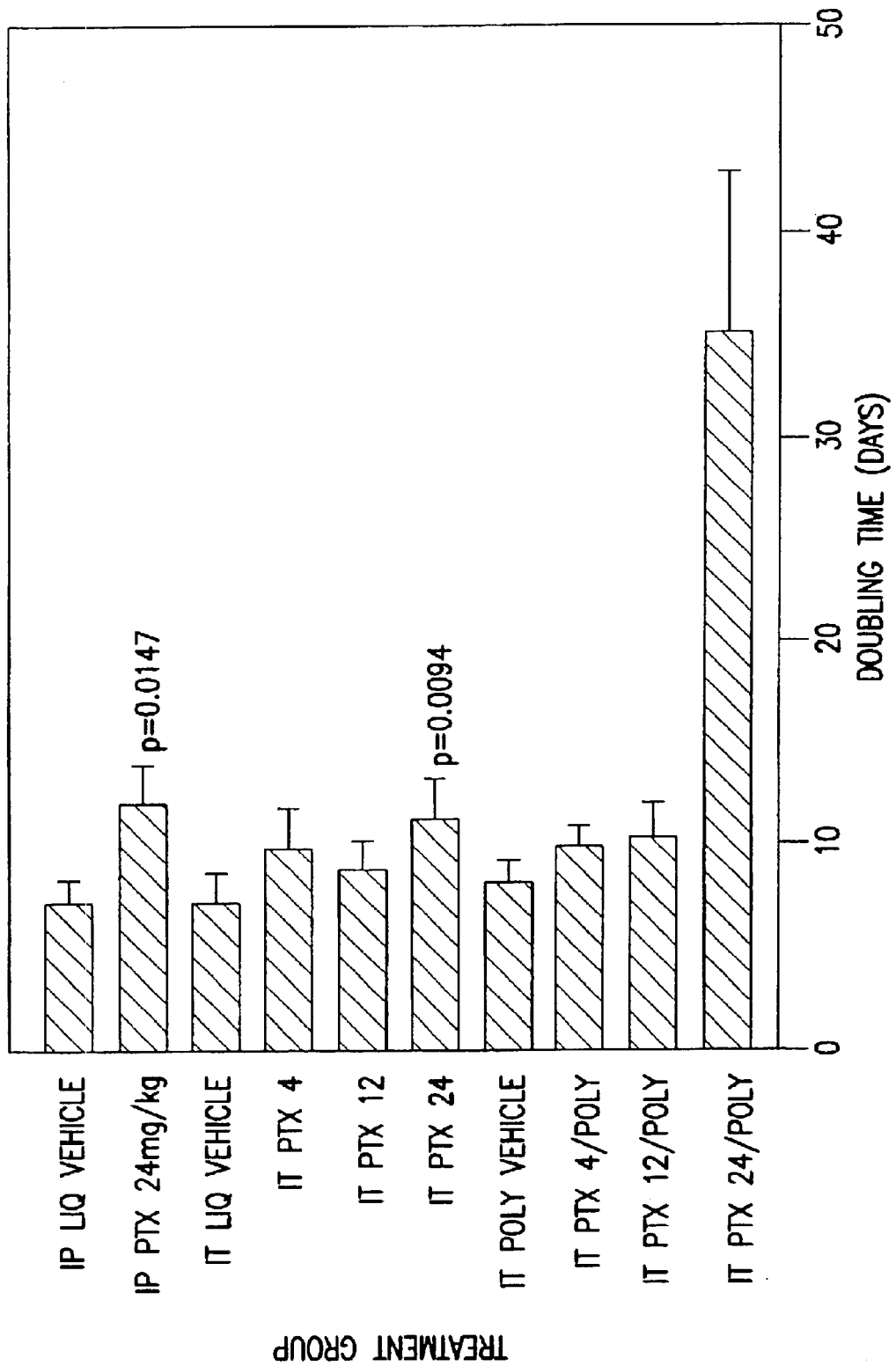
FIG. 12 shows the estimated tumor volume doubling times based on data derived from that shown in FIGS. 7–9 for H1299 tumor cells. P values shown represent the differences between the corresponding group and the 24 mg/kg group for paclitaxel in poly(DAPG-EOP).

The tumor volume doubling time was determined from the tumor measurements in all treatment groups. The results are presented graphically in FIG. 11 for treating A549 cell line tumors and in FIG. 12 for treating H1299 cell line tumors.

In the A549 cells, the doubling time of the paclitaxel in poly(DAPG-EOP) 24 mg/kg group was estimated at 60±9.4 days, compared to 11.5±2.3 days and 10.2±4.7 days for the conventionally formulated paclitaxel at 24 mg/kg given by the intraperitoneal and intratumoral routes respectively. The H1299 cell doubling time in the paclitaxel/poly(DAPG-EOP) 24 mg/kg group was estimated to be 35±8 days, compared to 12±1.9 and 11.2±1.9 days for conventionally formulated paclitaxel (24 mg/kg) given via the intraperitoneal and intratumoral routes respectively.

In summary, tumor volume doubling times of about 60 days for A549 nodules and about 35 days for H1299 nodules for 24 mg/kg paclitaxel in poly(DAPG-EOP) microspheres, as compared with 10 and 11 days respectively in the nodules treated with the same dosage level of conventional paclitaxel by intratumoral administration.

Example 22

Efficacy Against Other Solid Tumors

Cell lines representing the following types of carcinoma are obtained from the American Type Culture Collection, amplified in culture and engrafted into immunosuppressed mice, as described above:

| Cell Line | Carcinoma type |
|---|---|
| SCC-15 | Head and neck |
| FaDu | Head and neck |
| HEp2 | Laryngeal |
| WiDr | Colon |
| HT-29 | Colon |
| SW 837 | Rectum |
| SW 1463 | Rectum |

| Cell Line | Carcinoma type |
| --- | --- |
| PC-3 | Prostate |
| DU145 | Prostate |
| SK-Br-3 | Breast |
| MCF7 | Breast |
| 5637 | Bladder |
| T24 | Bladder |
| SK-MEL1 | Melanoma |
| SK-MEL2 | Melanoma |

A series of doses of the sustained release formulation of paclitaxel in poly(DAPG-EOP) microspheres at different dosage levels, including some higher than 24 mg/kg, are administered as specified above. Tumor volumes are followed over time. When compared with test animals receiving paclitaxel in the conventional cremophor/ethanol solution, the murine tumor nodule model demonstrates significant improvements in controlling multiple types of solid tumor growth, reducing the rate of growth and, in some cases, even reducing actual tumor size.

Example 23

Administration to Intrathoracic Masses

Extended release paclitaxel in poly(DAPG-EOP) microspheres is administered to lung cancer tumor masses, including a primary bronchogenic carcinoma and a carcinoma that has metastasized to the thorax. The paclitaxel-poly(DAPG-EOP) formulation is administered in single or multiple doses to the lung cancer tumor masses with a Turner Biopsy needle. A fluoroscope or CT (computerized tomography) is used for guidance. Dosages of 2–96 mg/kg can be used. Dosages can be based on body mass or on tumor volume. A comparison to intratumoral administration of the same dosage of paclitaxel in a conventional cremophor/ethanol solvent illustrate the unexpected benefits of the biodegradable poly(phosphoester) compositions and methods of the invention.

The invention being thus described, it will be obvious that the same may be varied in many ways. Such variations are not to be regarded as a departure from the spirit and scope of the invention, and all such modifications are intended to be included within the scope of the following claims.

We claim:

1. A biodegradable polymer composition suitable for intratumoral administration to a mammal having a solid tumor, said composition comprising:
   (a) a poly(phosphoester) biodegradable polymer;
   (b) at least one antineoplastic agent in an amount effective to inhibit the growth of said tumor when administered by intratumoral injection, wherein a single administration of a dose of the composition provides extended release of the antineoplastic agent over a time of at least one day.

2. The polymer composition of claim 1, wherein the inhibition of the growth of said solid tumor is measured as a delay in tumor doubling time.

3. The polymer composition of claim 2, wherein said tumor doubling time is extended by a factor of at least two.

4. The polymer composition of claim 2, wherein said tumor doubling time is extended by a factor of at least four.

5. The polymer composition of claim 1, wherein the inhibition of the growth of said solid tumor is measured by a reduction in the volume of said tumor.

6. The polymer composition of claim 5, wherein the volume of the tumor is reduced by at least about 10%.

7. The polymer composition of claim 5, wherein the volume of the tumor is reduced by at least about 30%.

8. The polymer composition of claim 5, wherein the volume of the tumor is reduced by at least about 50%.

9. The polymer composition of claim 5, wherein the volume of the tumor is reduced by at least about 70%.

10. The composition of claim 1, wherein said antineoplastic agent comprises a taxane.

11. The composition of claim 1, wherein said antineoplastic agent comprises paclitaxel.

12. The composition of claim 1, wherein the biodegradable polymer is a phosphoester co-ester.

13. The composition of claim 1, wherein a single dose of the composition provides extended release of the antineoplastic agent over a time of at least 15 days.

14. The composition of claim 1, wherein a single dose of the composition provides extended release of the antineoplastic agent over a time of at least 30 days.

15. The polymer composition of claim 1, wherein said polymer comprises the recurring monomeric units shown in formula I:

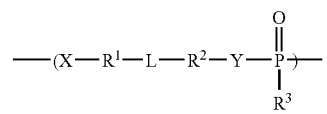

wherein X is —O— or —NR$^4$—;
Y is —O— or —NR$^4$—;
R$^4$ is H or alkyl;
each of R$^1$ and R$^2$ is a divalent organic moiety;
L is a divalent, branched or straight chain aliphatic group having 1–20 carbon atom, a cycloaliphatic group, or a group having the formula:

and R$^3$ is selected from the group consisting of H, alkyl, alkoxy, aryl, aryloxy, heterocyclic or heterocycloxy.

16. The polymer composition of claim 1, wherein said biodegradable poly(phosphoester) comprises monomeric units represented by formulas IV, V, VI and VII:

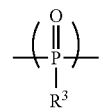

IV

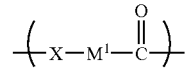

V

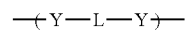

VI

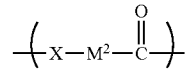

VII wherein X is —O— or —NR$^4$—;
Y is —O—, —S— or —NR$^4$—;

R⁴ is H or alkyl;

M¹ and M² are each independently (1) a branched or straight chain aliphatic group having from 1–20 carbon atoms; or (2) a branched or straight chain, oxy-, carboxy- or amino-aliphatic group having from 1–20 carbon atoms;

L is a divalent, branched or straight chain aliphatic group having 1–20 carbon atom; and R³ is selected from the group consisting of H, alkyl, alkoxy, aryl, aryloxy, heterocyclic or heterocycloxy.

17. The composition of claim 16, wherein said poly(phosphoester) has the formula VIII or IX:

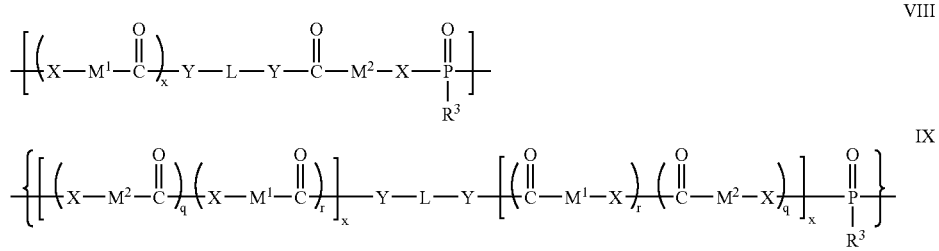

wherein M¹ and M² are each independently (1) a branched or straight chain aliphatic group having from about 1–20 carbon atoms; or (2) a branched or straight chain, oxy-, carboxy- or amino-aliphatic group having from about 1–20 carbon atoms;

L is a divalent, branched or straight chain aliphatic group having 1–20 carbon atoms;

the molar ratio of x:y is about one; and the molar ratio q:r varies between about 1:99 and 99:1.

18. The composition of claim 17, wherein R³ is an alkoxy group; X and Y are each oxygen; and M¹, M² and L are each independently a branched or straight chain alkylene group having from 1 to 7 carbon atoms.

19. The composition of claim 17, wherein R³ is an alkoxy group having from 1 to 7 carbon atoms; L is alkylene; and M¹ and M² are each independently an alkylene group having from 1 to 3 carbon atoms.

20. The composition of claim 17, 18 or 19, wherein the antineoplastic agent is a taxane.

21. The composition of claim 17, 18 or 19, wherein the antineoplastic agent is paclitaxel.

22. The polymer composition of claim 1, wherein said biodegradable poly(phosphoester) comprises monomeric units represented by formula X:

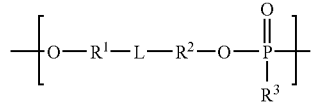

wherein each of R¹ and R² is independently straight or branched aliphatic, either unsubstituted or substituted with one or more non-interfering substituents; and L is a divalent cycloaliphatic group; and R³ is selected from the group consisting of H, alkyl, alkoxy, aryl, aryloxy, heterocyclic or heterocycloxy.

23. The composition of claim 22, wherein each of R¹ and R² is a methylene group; R³ is an alkoxy group having from 1 to 6 carbon atoms; and L is cyclohexylene.

24. The composition of claim 22 or 23, wherein the antineoplastic agent comprises a taxane.

25. The composition of claim 22 or 23, wherein said antineoplastic agent comprises paclitaxel.

26. The composition of claim 17 or 22, wherein the inhibition of the growth of said solid tumor is measured as a delay in tumor doubling time and is extended by a factor of at least two.

27. The polymer composition of claim 17 or 22, wherein the inhibition of the growth of said solid tumor is measured by a reduction in volume of said tumor, and the volume of the tumor is reduced by at least about 10%.

28. The composition of claim 17, or 22, wherein a single dose of the composition provides extended release of the antineoplastic agent over a time of at least 15 days.

29. The composition of claim 28, wherein said single dose of the composition provides extended release of the antineoplastic agent over a time of at least 30 days.

30. A biodegradable polymer composition suitable for intratumoral administration to treat a mammal having a solid tumor, said composition comprising:
   (a) a poly(phosphoester) biodegradable polymer made by the process of reacting a phosphorodihalidate and a diol; and
   (b) at least one antineoplastic agent in an amount effective to inhibit the growth of said tumor when administered by intratumoral injection,
   wherein a single administration of a dose of the composition provides extended release of the antineoplastic agent over a time of at least one day.

31. A biodegradable polymer composition suitable for intratumoral administration to treat a mammal having a solid tumor, said composition comprising:
   (a) at least one antineoplastic agent in an amount effective to inhibit the growth of said tumor when administered by intratumoral injection; and
   (b) a poly(phosphoester) biodegradable polymer made by a process comprising:
      (1) reacting at least one heterocyclic ring compound with H—Y-L-Y—H, wherein H is hydrogen; Y is —O—, —S— or —NR⁴—, where R⁴ is H or alkyl; and L is a divalent, branched or straight chain aliphatic group having 1–20 carbon atoms, to form a prepolymer;
      (2) further reacting the prepolymer with a phosphorodihalidate to form a poly(phosphoester),
   wherein a single administration of a dose of the composition provides extended release of the antineoplastic agent over a time of at least one day.

32. The composition of claim 31, wherein the inhibition of the growth of said solid tumor is measured by a reduction in the volume of said tumor, and the amount of said antineoplastic agent is sufficient to reduce the volume of the tumor by at least 10%.

33. The composition of claim 31, wherein the inhibition of the growth of said solid tumor is measured as a delay in tumor doubling time, and the tumor doubling time is extended by a factor of at least two.

34. An article suitable for the intratumoral administration of an antineoplastic agent to a mammal having a solid tumor wherein the article comprises:

(a) a biodegradable poly(phosphoester); and (b) at least one antineoplastic agent in an amount effective to inhibit the growth of said tumor when administered by intratumoral injection), wherein the article provides extended release of the antineoplastic agent over a time of at least one day.

35. The article of claim 34, wherein the inhibition of the growth of said solid tumor is measured by a reduction in the volume of said tumor, and the amount of said antineoplastic agent is sufficient to reduce the volume of the tumor by at least 10%.

36. The article of claim 34, wherein the inhibition of the growth of said solid tumor is measured as a delay in tumor doubling time, and the tumor doubling time is extended by a factor of at least two.

37. The article of claim 34, wherein said article is in the form of a needle, a rod, a stent, or injectable microparticles.

38. The article of claim 34, wherein said article is in the form of microspheres.

39. The composition of claim 1, wherein said composition is in the form of a viscous liquid, emulsion or suspension.

* * * * *

UNITED STATES PATENT AND TRADEMARK OFFICE
CERTIFICATE OF CORRECTION

PATENT NO. : 7,101,568 B2
APPLICATION NO. : 10/367292
DATED : September 5, 2006
INVENTOR(S) : Wenbin Dang and Robert Garver It is certified that error appears in the above-identified patent and that said Letters Patent is hereby corrected as shown below:

In claim 28, remove the comma following the number "17".

In claim 34, remove the parenthesis ")" following the word "injection."

Signed and Sealed this

Third Day of April, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,101,568 B2 | Page 1 of 1 |
| APPLICATION NO. | : 10/357292 | |
| DATED | : September 5, 2006 | |
| INVENTOR(S) | : Wenbin Dang and Robert Garver | |

It is certified that error appears in the above-identified patent and that said Letters Patent is hereby corrected as shown below:

In claim 28, remove the comma following the number "17".

In claim 34, remove the parenthesis ")" following the word "injection."

This certificate supersedes Certificate of Correction issued April 3, 2007.

Signed and Sealed this

Eighth Day of May, 2007

JON W. DUDAS
*Director of the United States Patent and Trademark Office*